(12) United States Patent
Spalding et al.

(10) Patent No.: US 12,097,346 B1
(45) Date of Patent: Sep. 24, 2024

(54) THORACOSTOMY DEVICE

(71) Applicant: OhioHealth Corporation, Columbus, OH (US)

(72) Inventors: Marshall Chance Spalding, Columbus, OH (US); Keshav Deshpande, Columbus, OH (US); Patrick D. Smith, Columbus, OH (US); Tony Mango, Columbus, OH (US); Lauren Shingler, Columbus, OH (US)

(73) Assignee: OhioHealth Corporation, Columbus, OH (US)

( * ) Notice: Subject to any disclaimer, the term of this patent is extended or adjusted under 35 U.S.C. 154(b) by 419 days.

(21) Appl. No.: 17/193,943

(22) Filed: Mar. 5, 2021

Related U.S. Application Data

(60) Provisional application No. 62/987,721, filed on Mar. 10, 2020.

(51) Int. Cl.
*A61M 27/00* (2006.01)

(52) U.S. Cl.
CPC ..... *A61M 27/002* (2013.01); *A61M 2027/004* (2013.01); *A61M 2205/04* (2013.01); *A61M 2205/587* (2013.01); *A61M 2210/101* (2013.01)

(58) Field of Classification Search
CPC ............ A61M 1/04; A61M 2202/0492; A61M 2210/1039; A61M 2039/0252; A61M 29/00; A61M 27/002; A61M 2027/004; A61M 2205/04; A61M 2205/587; A61M 2210/101; A61B 2017/00809;

(Continued)

(56) References Cited

U.S. PATENT DOCUMENTS 3,613,684 A * 10/1971 Sheridan ............ A61B 17/3415
128/207.29
3,742,958 A * 7/1973 Rundles ............ A61B 17/3417
604/164.05

(Continued)

FOREIGN PATENT DOCUMENTS

CN 105852940 A * 8/2016
CN 105769258 B * 6/2018

(Continued)

*Primary Examiner* — Adam Marcetich
(74) *Attorney, Agent, or Firm* — Ice Miller LLP

(57) ABSTRACT

A thoracostomy device that may be used for the placement of a chest tube is disclosed. The thoracostomy device is adapted to be extended into an incision in a patient, and comprises: (a) a handle portion; (b) an insertion portion extending from the handle portion, and having a linear portion and a curved terminal portion, the insertion portion having opposed substantially continuous first inner and second outer lateral surfaces, the device defining a central axis extending therethrough; and (c) a continuous channel extending through the handle and insertion portions and open to the first inner lateral surface, the channel having a medial axis offset from and parallel to the central axis, the channel adapted to guide a tube along the central axis while being adapted to allow a tube to be removed laterally of the channel. The present invention also includes a method of preparing a chest tube for insertion and for inserting a chest tube such as through the use any of the devices of the present invention.

20 Claims, 34 Drawing Sheets

(58) Field of Classification Search
CPC .......... A61B 2018/00541; A61B 17/34; A61B 17/3415; A61B 17/3417; A61B 2017/3427
See application file for complete search history.

(56) References Cited

U.S. PATENT DOCUMENTS

| | | | | | |
|---|---|---|---|---|---|
| 4,211,234 | A * | 7/1980 | Fisher | ............... | A61M 16/0429 128/200.26 |
| 4,617,929 | A * | 10/1986 | Gill | ............... | A61B 17/3439 128/207.29 |
| 5,071,408 | A * | 12/1991 | Ahmed | ............... | A61F 9/00781 604/9 |
| 5,380,290 | A * | 1/1995 | Makower | .......... | A61M 25/0662 604/164.01 |
| 5,645,519 | A * | 7/1997 | Lee | .................... | A61B 1/2676 600/185 |
| 5,713,868 | A * | 2/1998 | Fussman | ........... | A61M 25/0662 604/164.01 |
| 5,853,391 | A * | 12/1998 | Bell | .................... | A61B 17/3401 604/164.11 |
| 6,200,321 | B1 * | 3/2001 | Orbay | ................ | A61B 17/1686 606/96 |
| 6,606,515 | B1 * | 8/2003 | Windheuser | ......... | A61M 25/02 600/585 |
| 6,761,725 | B1 * | 7/2004 | Grayzel | ............... | A61B 17/282 606/174 |
| 2003/0187461 | A1 * | 10/2003 | Chin | .................. | A61B 1/00094 606/129 |
| 2006/0025779 | A1 * | 2/2006 | Dutcher | ............. | A61B 17/3415 606/108 |
| 2007/0276288 | A1 * | 11/2007 | Khaw | ............. | A61M 25/09041 604/164.13 |
| 2009/0032016 | A1 * | 2/2009 | Law | ................... | A61B 1/00052 128/207.14 |
| 2009/0320854 | A1 * | 12/2009 | Cuevas | ................ | A61M 29/00 128/207.29 |
| 2012/0071856 | A1 * | 3/2012 | Goldfarb | ............ | A61M 25/0113 604/514 |
| 2012/0204867 | A1 * | 8/2012 | Levitan | ............ | A61M 16/0472 128/200.26 |
| 2013/0131549 | A1 * | 5/2013 | Kristensen | ......... | A61B 17/3415 600/581 |
| 2015/0133952 | A1 * | 5/2015 | Seifert | ............... | A61B 17/3415 607/116 |
| 2017/0296797 | A1 * | 10/2017 | Hill | .................... | A61B 17/2841 |
| 2020/0289155 | A1 * | 9/2020 | McDonnall | ............. | A61N 1/05 |
| 2021/0015674 | A1 * | 1/2021 | Frölich | .................. | A61F 11/20 |

FOREIGN PATENT DOCUMENTS

| | | | | | |
|---|---|---|---|---|---|
| EP | | 1201263 | A2 * | 5/2002 | ......... A61B 17/3415 |
| GB | | 2142244 | A * | 1/1985 | ......... A61B 17/3439 |
| WO | WO-0106938 | A1 * | 2/2001 | ..... A61B 17/320036 |

* cited by examiner

THORACOSTOMY DEVICE

CROSS-REFERENCE TO RELATED APPLICATIONS

This Application claims the priority benefit of U.S. Provisional Application No. 62/987,721, filed Mar. 10, 2020, and hereby incorporates by reference U.S. Provisional Application Ser. No. 62/823,427, filed Mar. 25, 2019, both of which are hereby incorporated in their entirety herein by reference.

FIELD

The present disclosure relates generally to a thoracostomy device and, more particularly, to a device that is used to aid in ventilating a patient through insertion of a chest tube.

BACKGROUND

This present invention relates to and may be applied in current thoracostomy procedures wherein typically a small incision is made in the chest wall, which opening is maintained for drainage.

Thoracostomy procedures are normally performed by physicians or paramedics, usually via a needle thoracostomy or with a thoracostomy tube. The thoracostomy procedure typically involves inserting a hollow tube into the chest cavity in order to drain air, fluid, and blood to relieve pressure on the lungs and heart.

It is most commonly used for the treatment of a pneumothorax, though may be applied for other purposes and therapeutic effects.

Chest tubes are one of the most common cardio-thoracic procedures performed. These tubes are placed to drain air, fluid or blood from the chest cavity and relieve pressure on the lungs and heart. Chest tubes are placed primarily by surgeons from residency through attending physicians, but they can also be placed by emergency medicine physicians, nurse practitioners and physician assistants. The global market value of chest tubes is $555.8 million with CAGR of 6%. Nationally the chest tube market is valued at $215.1 million. See "Thoracic Drainage Devices Market—Global Industry Analysis, Size, Share, Growth, Trends, & Forecast 2017-2025." *Transparency Market Research*, March 2018.

Of the million chest tubes placed nationally each year, the procedure has a complication rate of 20-35% due to insertional (14%), positional (69%), and post-removal (17%) errors. On average, the costs of the procedure are 9 times higher, with insertional errors attributing to as much as 21× higher costs. See Hernandez, M C, et al. "Tube Thoracostomy Complications Increase Cost." *World Journal of Surgery*, U.S. National Library of Medicine, June 2017. It is estimated that complications due to chest tube procedures are an issue costing $40 billion annually in the U.S., with $22.6 million in annual costs for OhioHealth.

One of the principal problems in current thoracostomy procedures is that the common procedure has a complication rate ranging from 20-35%. See Hernandez, M C, et al. "Tube Thoracostomy Complications Increase Cost." *World Journal of Surgery*, U.S. National Library of Medicine, June 2017. The complications of the procedure fall into three major categories: insertional, positional, and post-removal.

Insertional complications are the most severe, resulting in immediate injury and resulting in costs 21 times higher than a normal procedure. These complications only account for 14% of total complications; however they present the greatest threat to effective patient care.

Positional complications such as kinking, tube obstruction, and incorrect placement result in only 3 times higher costs but account for nearly 70% of all thoracostomy complications. Issues that occur during post-removal, such as insertion site infection, account for 17% of complications and result in costs 3 times higher than normal. See Hernandez, M C, et al. "Tube Thoracostomy Complications Increase Cost." *World Journal of Surgery*, U.S. National Library of Medicine, June 2017.

For instance, in one hospital placing around 570 chest tubes per year, the complication rate results in up to 200 of these placements encountering some type of complication. A rate this high for any surgical procedure is unacceptable, and the present invention is directed to a solution that allows for first-attempt correct insertion and placement of the chest tube in order to reduce complications and therefore lower costs to the hospital and improve patient care.

A step-by-step process of the procedure and the possible errors that may occur, shown in Table 1 below. These errors can be due to poor design of equipment, the size of the patient, the size of the physician, the technique used, and the situation. One common theme that most doctors experience is an unnamed webbing tissue that connects the lung to the pleura and forces the chest tube into the fissure without the physician noticing or feeling it. The webbing only exists in some patients, and an example diagram of it is in the appendix (Figure A1). Another popular theme amongst physicians is that performing the procedure on obese patients is very difficult in the majority of steps below.

TABLE 1

Steps in the thoracostomy procedure aligned with potential errors and resulting product requirements.

| Step in Procedure | Possible Errors | Product Requirement |
|---|---|---|
| Placement, dissection, anesthetic | Going too superior/ inferior Obese patients | Device should be less dependent on location of incision than current technique |
| Dissection up and over rib | Difficult for obese patients Small hand/finger size Cluttered with large hands Locate incorrect rib | Device should locate the correct rib with minimal effort and space required |
| Puncturing pleura, dilating tract | Tough on fingers Kelly's not used well- not a big enough hole made Dissect too far | Device should dissect pleura and remove additional webbing with little effort |
| Finding same tract with finger | Lose tract Cluttered environment Finger sweep doesn't detect webbing | Device should minimize space required to retain the tract and/or not require a hand to hold the place |
| Directing and positioning chest tube | Go into fissure Kink/bend Not placed at superior apex | Device should direct placement into superior apex without kinks |
| Suturing tube in place | Different techniques Infection Pulled out | Standardize suturing with device or technique |

Therefore, there has been a long-felt but unresolved need for a thoracostomy device that provides relatively higher first-attempt correct insertion and placement of the chest tube, as well as proper positioning of the patient's jaw, during ventilation.

SUMMARY OF THE INVENTION

The present invention includes a handheld thoracostomy device for thoracic blunt dissection, pleural cavity clearance, and guided placement of a tube thoracostomy.

Device Claims Directed to Basic Geometry of Device and Insertion Function

In one general embodiment, the present invention may include a thoracostomy device adapted to be extended into an incision in a patient, comprising: (a) a handle portion; (b) an insertion portion extending from the handle portion, and having a linear portion and a curved terminal portion, the insertion portion having opposed substantially continuous first inner and second outer lateral surfaces, the device defining a central axis extending therethrough, and (c) a continuous channel extending through the handle and insertion portions and open to the first inner lateral surface, the channel having a medial axis offset from and parallel to the central axis, the channel adapted to guide a tube along the central axis while being adapted to allow a tube to be removed laterally of the channel.

The continuous channel extending through the handle and insertion portions will be sized so as to be able to hold a flexible tube generally parallel to the central axis of the device and to extend though the curved terminal portion thereof, and to do so while the device is used to inert and place the chest tube.

In some alternative embodiments, the width of the handle portion may be greater than the width of the insertion portion.

In some alternative embodiments, the handle portion comprises a main portion and a relatively minor distally tapered portion, tapered toward the insertion portion.

In other alternative embodiments, the minor distally tapered portion comprises an offset frustoconical shape.

In other alternative embodiments, the surface of the relatively minor distally tapered portion is continuous with the second outer lateral surface, to permit smooth insertions and extraction of the device from the chest cavity.

The continuous channel is preferably sized so as to have its channel opening width be slightly less than the diameter of the chest tube to be used, so as to maintain the chest tube during insertion and placement, while still being adapted to permit lateral release of the chest tube from the channel by hand force following placement of the tube; and may be determined by reference to the chest tube material, its flexibility and the compressibility of the chest tube. In some alternative embodiments, the channel has a cross-section defining an arc of from about 210 degrees to about 325 degrees, while in other embodiments the channel has a cross-section defining an arc of from about 250 degrees to about 290 degrees.

In other alternative embodiments, the linear portion is relatively greater in length than the curved terminal portion.

In still other embodiments, the linear portion is tapered toward the curved terminal portion.

In other alternative embodiments, the linear portion having a longitudinal axis, wherein the curved terminal portion is sufficiently curved so as to provide a defection of its terminal end from about 5 degrees to about 35 degrees from the longitudinal axis of the linear portion, and preferably from about 10 degrees to about 30 degrees from the longitudinal axis of the linear portion, and most preferably about 17.5 degrees.

In other alternative embodiments, the handle portion may be formed so as to have a compartment adapted to contain a medical instrument, such as a scalpel that may be deployed from the device for convenient use during a surgical procedure. The compartment may be formed through the use of known mechanical arrangements and molding techniques applied to materials such as plastics and metals, such as through the use of hollow portions of the handle of appropriate sixe, and with according snap-fit or screw fit doors or lids to secure the contents.

Medical instruments that may be contained may also include prefilled syringes with syringe barrels prefilled with a drug, needles, suture materials, blood collection bags, blood collection instruments, and catheters, and other sterilized medical instruments, aseptically packaged; as well as pharmaceutical products such as vial bottles, etc.

In other alternative embodiments, wherein the handle portion additionally comprises a releasable container adapted to contain a medical instrument and/or flexible tube. The releasable container may be adapted to be releasable from the handle portion, such as through any manner of interference fit, screw or snap fitting, etc. through the use of known mechanical arrangements and molding techniques applied to materials such as plastics and metals.

The releasable container may be to any degree hollow so as to be adapted to contain a flexible tube that may be deployed for use in association with the device of the present invention.

In some embodiments, the releasable container may contain a flexible tube, such as in a coiled configuration.

Such arrangements may be of particular benefit for field surgery operations, and the medical instrument may be packaged to preserve sterility in accordance with known packaging techniques.

In other embodiments, the handle portion additionally may comprise a light source, such as one directed toward the curved terminal portion. Similar, in other embodiments, wherein the inner channel surface may comprise a light source directed toward the curved terminal portion within the channel. These light sources may be in the form of battery-operated (rechargeable or otherwise) light contained or ensconced into the handle or channel surface, in accordance with known designs for providing switch operated light sources in metallic or plastic articles. The wiring and switching may be incorporated into the device by known designs and methods commonly known and used in the field of surgical instruments.

More Specific Device Claims Based Upon Geometry of Device and Insertion Function In further embodiments, the present invention may include a thoracostomy device adapted to be extended into an incision in a patient, comprising: (a) a handle portion; (b) an insertion portion extending from the handle portion, and having a linear portion and a curved terminal portion, the insertion portion having opposed substantially continuous first inner and second outer lateral surfaces, the linear portion having a longitudinal axis, wherein the curved terminal portion is sufficiently curved so as to provide a defection of its terminal end from about 5 degrees to about 35 degrees from the longitudinal axis of the linear portion; the device defining a central axis extending therethrough, and (c) a continuous channel extending through the handle and insertion portions and open to the first inner lateral surface, the channel having a medial axis offset from and parallel to the central axis, the channel adapted to guide a tube along the central axis while being adapted to allow a tube to be removed laterally of the channel, wherein the channel has a cross-section defining an arc of from about 210 degrees to about 325 degrees.

More Specific Device Claims Based Upon Geometry of Device and Insertion Function and Addition of Light, Scalpel Compartment & Deployable Contained Chest Tube In still further embodiment, the present invention may include a thoracostomy device adapted to be extended into an incision in a patient, comprising: (a) a handle portion; (b) an insertion portion extending from the handle portion, and having a linear portion and a curved terminal portion, the insertion portion having opposed substantially continuous first inner and second outer lateral surfaces, the device defining a central axis extending therethrough, and (c) a continuous channel extending through the handle and insertion portions and open to the first inner lateral surface, the channel having a medial axis offset from and parallel to the central axis, the channel adapted to guide a tube along the central axis while being adapted to allow a tube to be removed laterally of the channel; and (d) the handle portion having a compartment adapted to contain a medical instrument, such as a scalpel.

The thoracostomy device of claim 1, wherein the handle portion having a compartment adapted to contain a scalpel or other medical instrument. The handle portion may be formed so as to allow access to one or more longitudinally extending interior spaces to form one or more such compartments, and these compartments may be configured to accommodate specific medical instruments.

In some embodiments, the invention includes a thoracostomy device adapted to be extended into an incision in a patient, comprising: (a) a handle portion; (b) an insertion portion extending from the handle portion, and having a linear portion and a curved terminal portion, the insertion portion having opposed substantially continuous first inner and second outer lateral surfaces, the device defining a central axis extending therethrough, and (c) a continuous channel extending through the handle and insertion portions and open to the first inner lateral surface, the channel having a medial axis offset from and parallel to the central axis, the channel adapted to guide a tube along the central axis while being adapted to allow a tube to be removed laterally of the channel; and (d) the handle portion having a compartment adapted to contain a flexible tube.

In other embodiments, the present invention may include a thoracostomy device adapted to be extended into an incision in a patient, comprising: (a) a handle portion; (b) an insertion portion extending from the handle portion, and having a linear portion and a curved terminal portion, the insertion portion having opposed substantially continuous first inner and second outer lateral surfaces, the device defining a central axis extending therethrough, and (c) a continuous channel extending through the handle and insertion portions and open to the first inner lateral surface, the channel having a medial axis offset from and parallel to the central axis, the channel adapted to guide a tube along the central axis while being adapted to allow a tube to be removed laterally of the channel; and (d) the handle portion additionally comprising a releasable container adapted to contain a flexible tube having a compartment adapted to contain a flexible tube.

Such embodiments likewise may include the releasable container containing a flexible tube as described herein.

In some embodiments, the invention includes a thoracostomy device adapted to be extended into an incision in a patient, comprising: (a) a handle portion; (b) an insertion portion extending from the handle portion, and having a linear portion and a curved terminal portion, the insertion portion having opposed substantially continuous first inner and second outer lateral surfaces, the device defining a central axis extending therethrough, and (c) a continuous channel extending through the handle and insertion portions and open to the first inner lateral surface, the channel having a medial axis offset from and parallel to the central axis, the channel adapted to guide a tube along the central axis while being adapted to allow a tube to be removed laterally of the channel; and (d) the handle portion additionally comprising a light source directed toward the curved terminal portion.

In still other alternative embodiments, the invention includes a thoracostomy device adapted to be extended into an incision in a patient, comprising: (a) a handle portion; (b) an insertion portion extending from the handle portion, and having a linear portion and a curved terminal portion, the insertion portion having opposed substantially continuous first inner and second outer lateral surfaces, the device defining a central axis extending therethrough, and (c) a continuous channel extending through the handle and insertion portions and open to the first inner lateral surface, the channel having a medial axis offset from and parallel to the central axis, the channel adapted to guide a tube along the central axis while being adapted to allow a tube to be removed laterally of the channel; and (d) wherein the channel comprises an inner channel surface that comprises a light source directed toward the curved terminal portion. More Specific Device Claims Based Upon Geometry of Device and Tube Compartment & Deployable Contained Chest Tube In still other embodiments, the invention includes a thoracostomy device adapted to be extended into an incision in a patient, comprising: (a) a handle portion; (b) an insertion portion extending from the handle portion, and having a linear portion and a curved terminal portion, the insertion portion having opposed substantially continuous first inner and second outer lateral surfaces, the device defining a central axis extending therethrough, and (c) a continuous channel extending through the handle and insertion portions and open to the first inner lateral surface, the channel having a medial axis offset from and parallel to the central axis, the channel adapted to guide a tube along the central axis while being adapted to allow a tube to be removed laterally of the channel; and (d) the handle portion additionally comprising a releasable container adapted to contain a flexible tube having a compartment adapted to contain a flexible tube, and (e) the releasable container containing a flexible tube.

Other aspects of the invention embodiment include that the length of the button or button panels, may be such so as to extend along a substantial portion of the tubular handle portion outer surface, and the button or button panels may be hinged with respect to the outer surface through any effective construction such as through the use of a flexible attachment portion on one end thereof, or a mechanical hinge.

Another embodiment of the invention features the tubular handle portion, having an interior surface, having the device hinge attached to the interior surface. In these or alternative embodiments, the tubular handle portion, having an interior surface and defining a longitudinally extending interior space, will have the hinge and opposed actuation arms mounted within the tubular handle portion so as to allow the longitudinally extending interior space to accommodate the passage of a longitudinally extending flexible extension member or probe to be extended through the tubular handle portion for use during the chest tube placement procedure.

In other embodiments of the invention, the handle portion additionally includes a longitudinally extending flexible extension member or probe extending therethrough.

Another embodiment of the invention may be summarized as a thoracostomy device adapted to be extended into an incision in a patient, comprising placing the insertion portion in a patient's chest cavity and using the device to insert and position a chest tube, followed by removing the chest tube from its contained position within the device channel.

The present invention also includes a method of preparing a chest tube for insertion and for inserting a chest tube such as through the use any of the devices of the present invention.

The method generally include loading a chest tube into a longitudinal channel of an insertion device such as that described herein (featuring a longitudinal channel adapted for the lateral release of a chest tube once directed and placed), and inserting a chest tube for placements in the chest cavity, followed by removal of the chest tube from its contained position within the device channel, such as through hand force by overcoming the positional static force holding the chest tube in the device channel.

Once the device loaded with the chest tube is inserted, the operator will be able to either twist the handle to rotate the insertion portion to perform the "finger" sweep that is typically done by hand. The smooth outer surface will be able to sweep the area without damaging the lung, while also giving some haptic feedback due to the operator.

Once the sweep is performed using the insertion portion, the insertion portion may remain in the pleura and may be used to guide the chest tube into the superior apex of the lung cavity. The material may be shaped similar to a semicircular cross-section that may advantageously fit through the remaining diameter of the tubular handle portion not otherwise occupied by the balance of the hinged mechanism. Thus, once the sweep is performed, the operator may be able to rotate the insertion portion into the correct location to guide the tube (such as may be indicated by haptic feedback, either visually or tactilely).

The operator will then be able to begin to insert the chest tube into the incision made in the body and follow along the channel of the insertion portion into the cavity.

Upon proper placement of the tube, the operator can slowly remove the device from the patient's body.

Once the device is removed, the thoracostomy procedure proceeds as typically planned, by suturing and attaching the tube to the suction device.

Thus, this device will allow for blunt dissection of the chest wall, maintaining the resultant tract in an open position, and the performance of a mechanical "finger sweep" without insertion of an operator's hand, and permit guidance of the tube into the correct location.

These aspects of the task typically are points of principal challenge and potential error in the intubation process that often lead to the high rates of complication in a thoracostomy procedure.

The present invention thus allows for the reduction of insertional and verification errors in the thoracostomy procedure in a non-emergent setting, in order to reduce patient complications and decrease associated medical costs.

BRIEF DESCRIPTION OF THE DRAWINGS

The present embodiments may be understood from the following detailed description when read in conjunction with the accompanying figures. It is emphasized that the various features of the figures are not necessarily to scale. On the contrary, the dimensions of the various features may be arbitrarily expanded or reduced.

DETAILED DESCRIPTION

Embodiments of the invention will now be described with reference to the figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

One embodiment of the device of the present invention is shown in the following FIGS. 1 through 18 wherein like numerals refer to the same portions and features.

Figure 1:
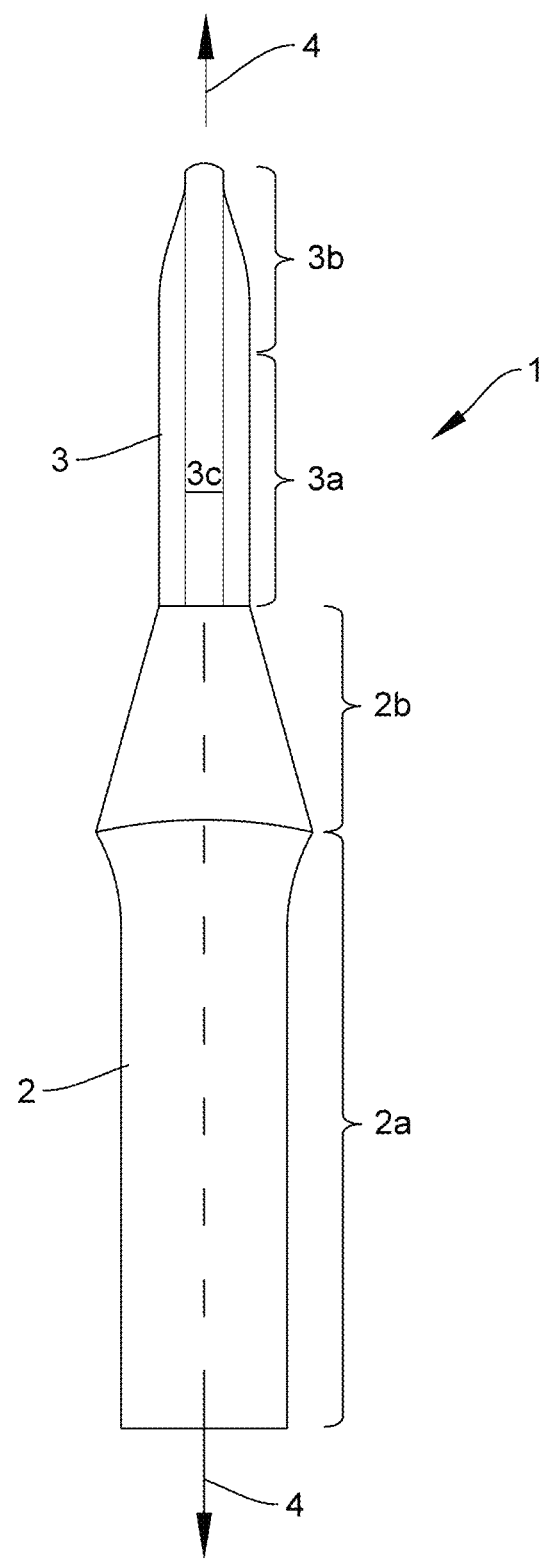
FIG. 1 shows a digital rendering of a thoracostomy device generally from a rear elevation view, in accordance with one embodiment of the invention.
Figure 2:
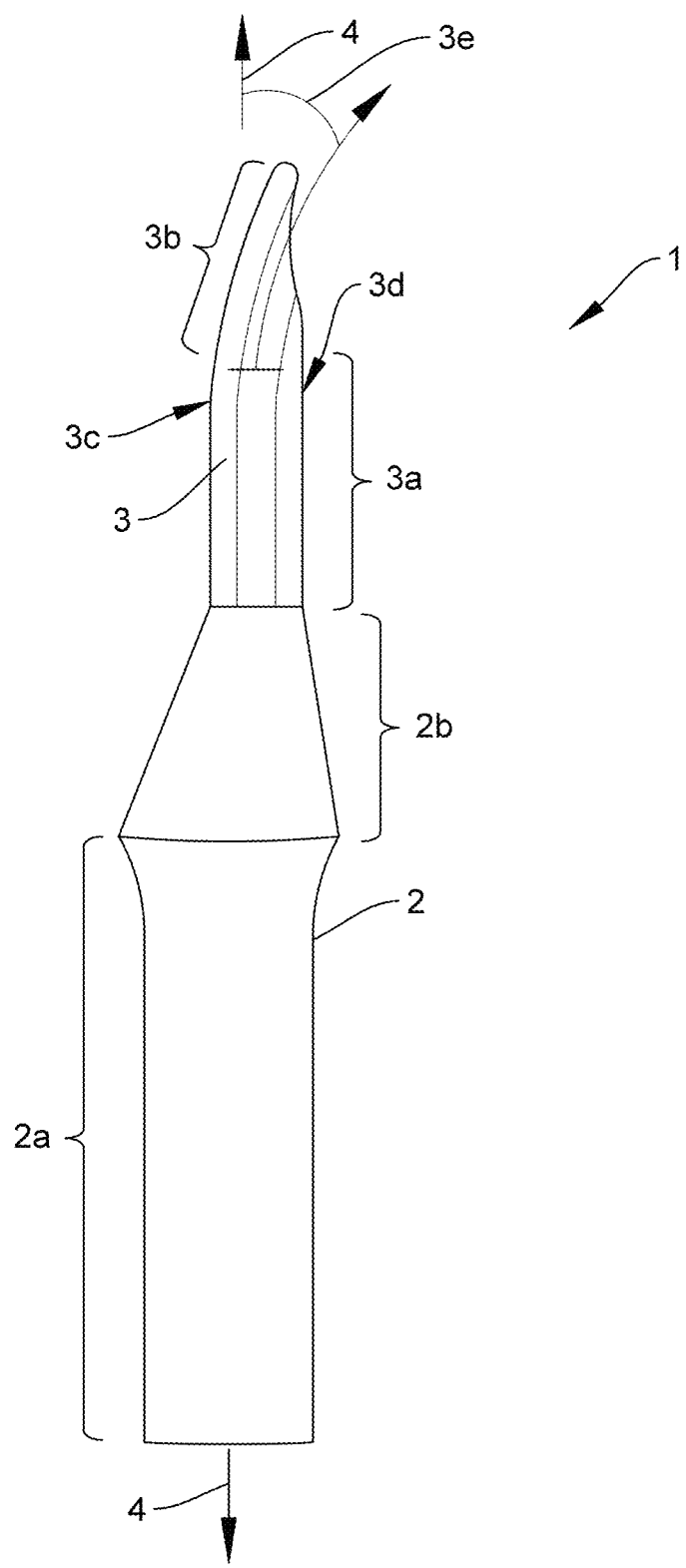
FIG. 2 shows a digital rendering of a thoracostomy device generally from a first lateral elevation view, in accordance with one embodiment of the invention.
Figure 3:
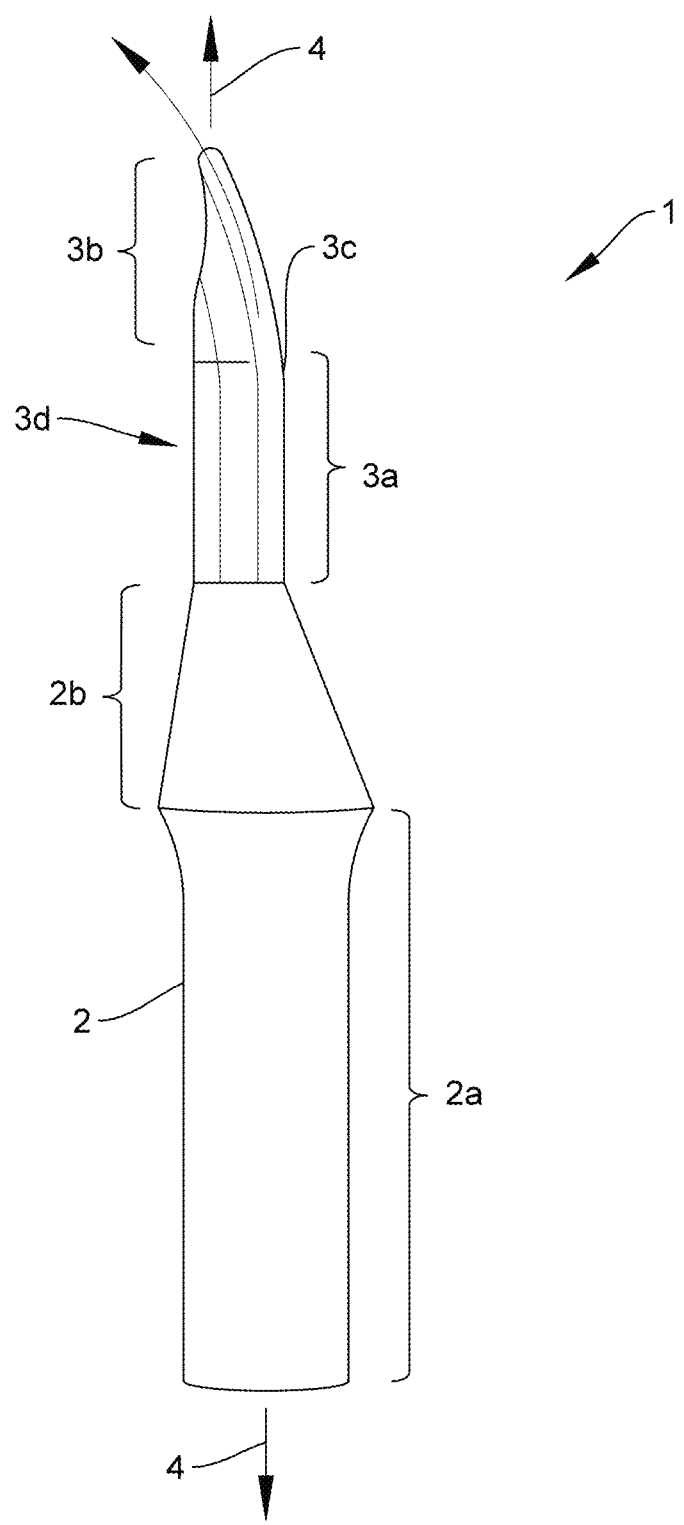
FIG. 3 shows a digital rendering of a thoracostomy device generally from a second lateral elevation view, opposite the first lateral elevation view, in accordance with one embodiment of the invention.

FIG. 1 shows a digital rendering of a thoracostomy device 1 generally from a rear elevation view, while FIG. 2 shows a digital rendering of a thoracostomy device 1 generally from a first lateral elevation view, and FIG. 3 shows a digital rendering of a thoracostomy device 1 generally from a second lateral elevation view, opposite the first lateral elevation view.

A thoracostomy device 1 adapted to be extended into an incision in a patient, comprising a handle portion 2 and an insertion portion 3 extending from the handle portion 2, and the insertion portion 3 having a linear portion 3a and a curved terminal portion 3b, the insertion portion having opposed substantially continuous first inner and second outer lateral surfaces 3d and 3c, respectively.

The thoracostomy device 1 defines a central axis 4 extending therethrough, and a continuous channel 5 extending through the handle 2 and insertion portion 3 and open to the first inner lateral surface 3d, the channel 5 having a medial axis 6 offset from and parallel to the central axis 4, the channel 5 adapted to guide a tube (not shown) along the medial axis 6 while being adapted to allow a tube to be removed laterally of the channel 5.

The thoracostomy device 1 is adapted to be extended into an incision in a patient and used to assist the placement of a chest tube therein.

Figure 4:
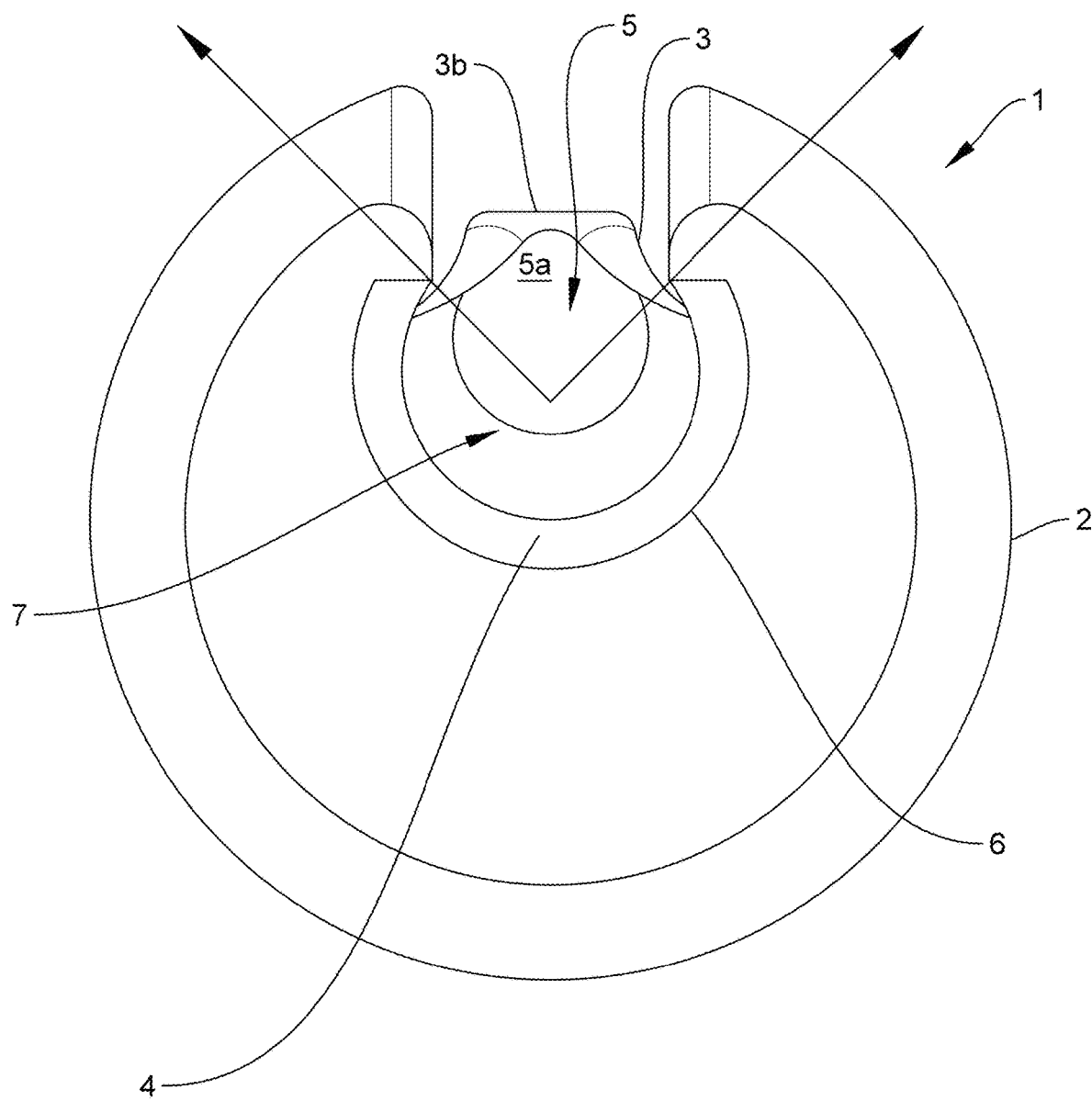
FIG. 4 shows a digital rendering of a thoracostomy device generally from a bottom plan view, in accordance with one embodiment of the invention.

FIG. 4 shows a digital rendering of a thoracostomy device 1 generally from a bottom plan view. This view shows channel 5 having a medial axis 6 offset from and parallel to the central axis 4, the channel 5 adapted to guide a tube (not shown) along the medial axis 6 while being adapted to allow a tube to be removed laterally of the channel 5. Although shown as having a cylindrical shape with a circular cross-section, the handle portion may be of any shape or cross-section, such as polygonal, ovoid or irregular shape, depending upon manufacturing efficiencies and ergonomic considerations.

Figure 5:
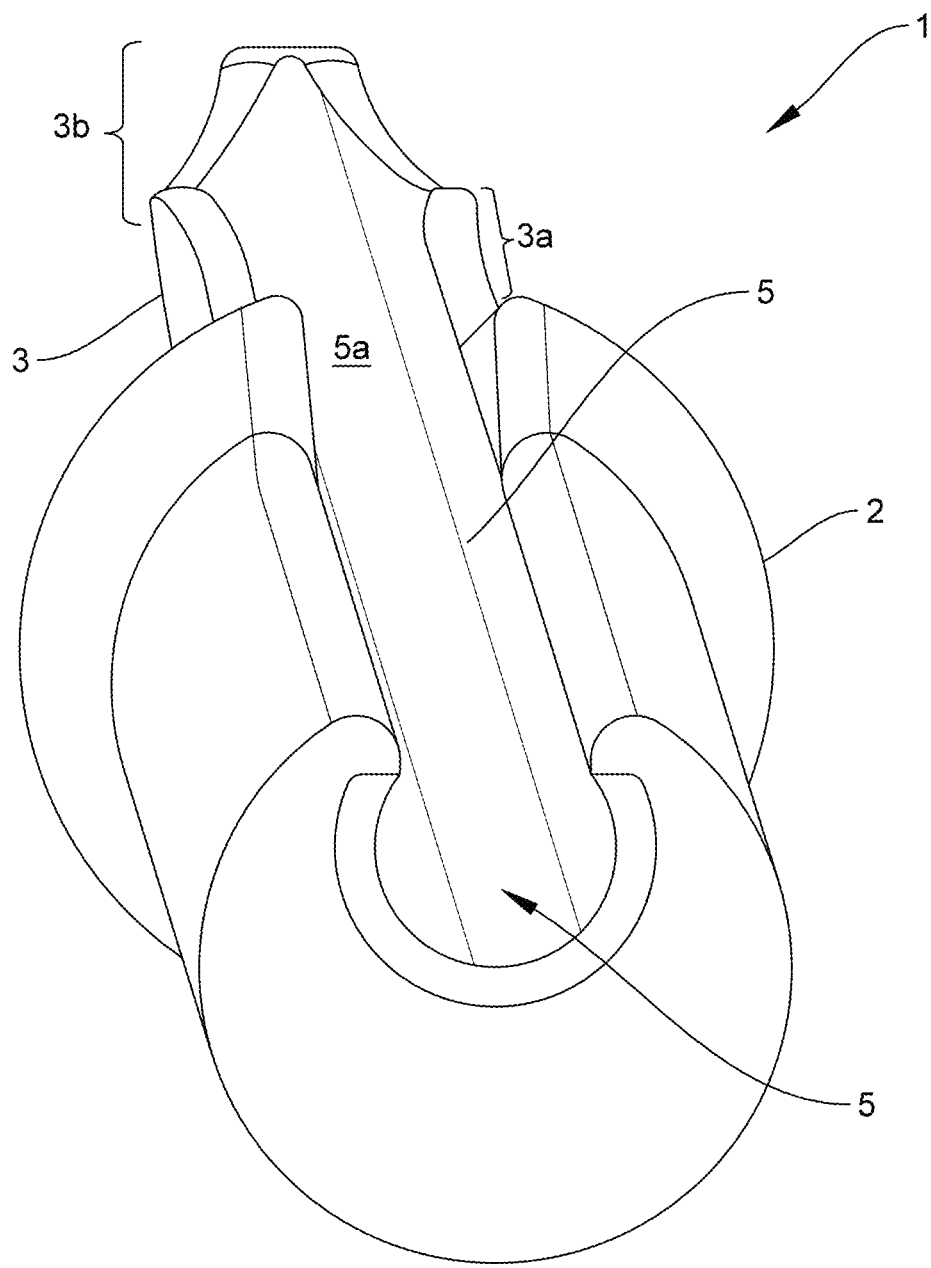
FIG. 5 shows a digital rendering of a thoracostomy device generally from a bottom front perspective view, in accordance with one embodiment of the invention.

FIG. 5 shows a digital rendering of a thoracostomy device 1 generally from a bottom front perspective view. This view also shows channel 5 having a medial axis 6 offset from and parallel to the central axis 4, the channel 5 adapted to guide a tube (not shown) along the medial axis 6 while being adapted to allow a tube to be removed laterally of the channel 5, in accordance with one embodiment of the invention.

Figure 6:
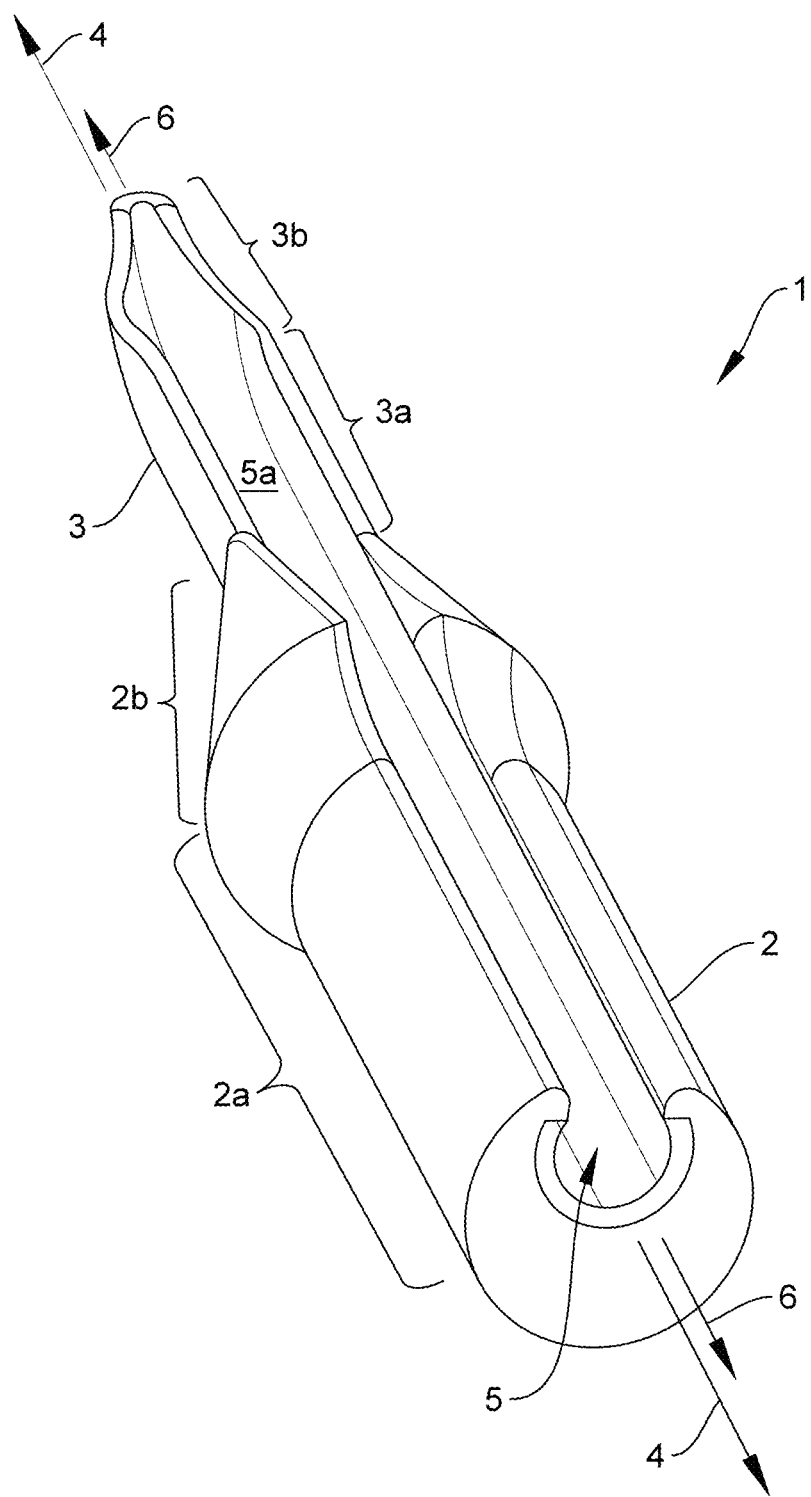
FIG. 6 shows a digital rendering of a thoracostomy device generally from a lower front perspective view, in accordance with one embodiment of the invention.

FIG. 6 shows a digital rendering of a thoracostomy device 1 generally from a lower front perspective view.

Figure 7:
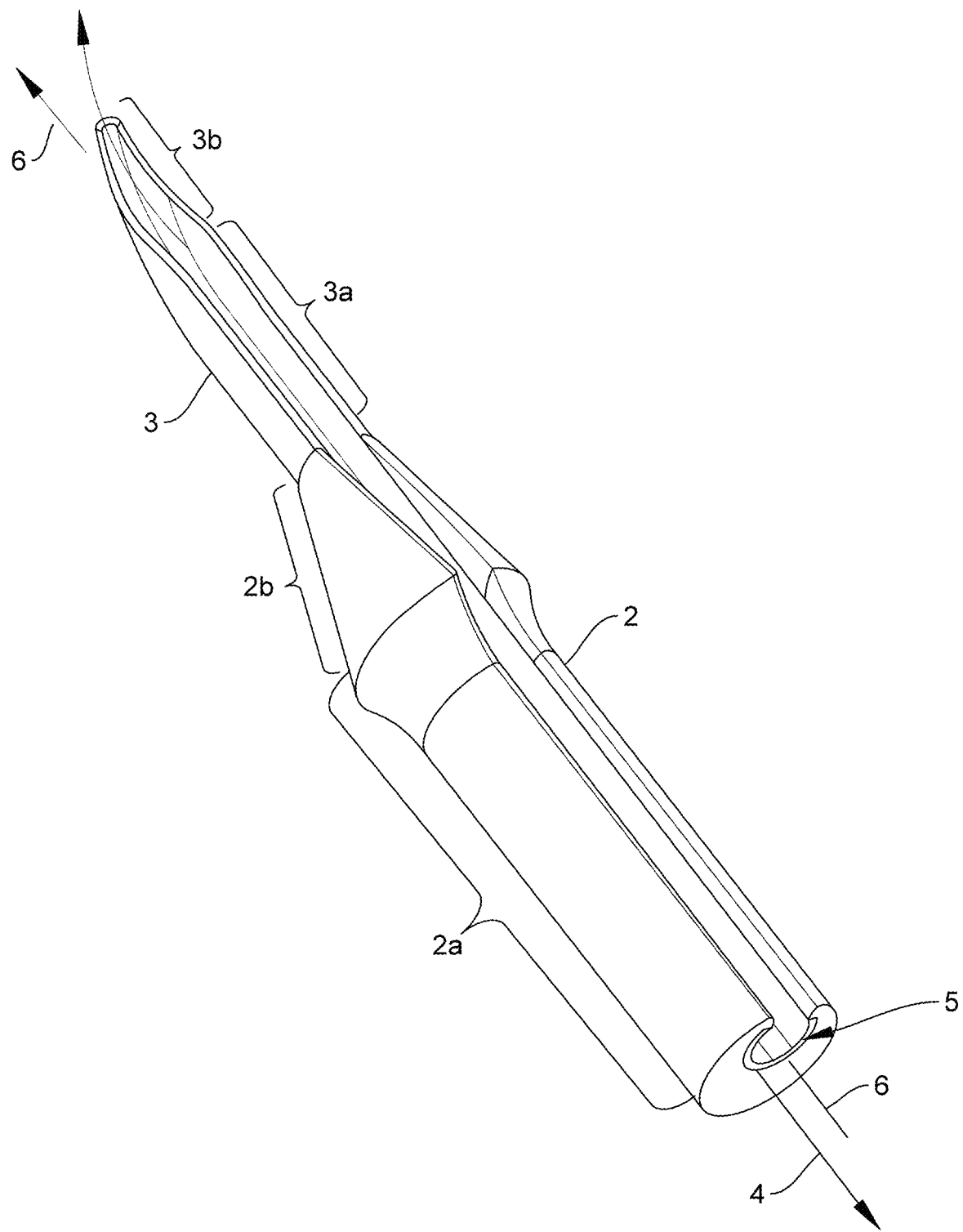
FIG. 7 shows a digital rendering of a thoracostomy device generally from a lateral front perspective view, in accordance with one embodiment of the invention.

FIG. 7 shows a digital rendering of a thoracostomy device 1 generally from a lateral front perspective view.

Figure 8:
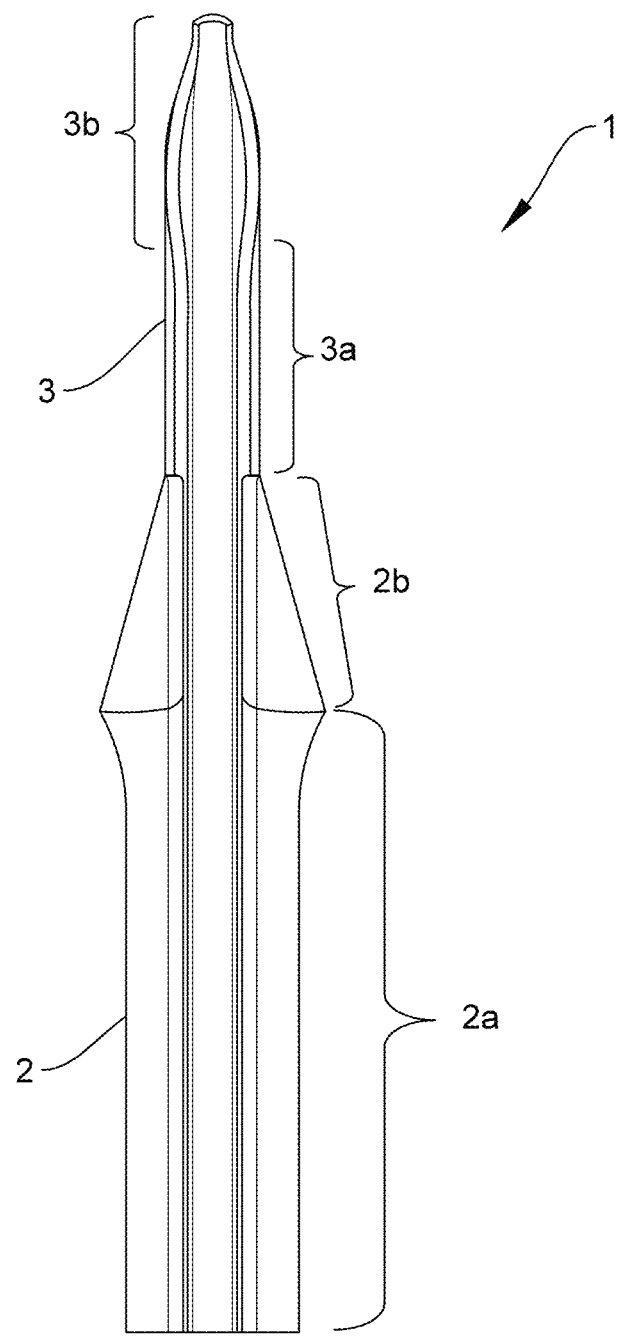
FIG. 8 shows a digital rendering of a thoracostomy device generally from a front elevation view, in accordance with one embodiment of the invention.

FIG. 8 shows a digital rendering of a thoracostomy device 1 generally from a front elevation view.

Figure 9:
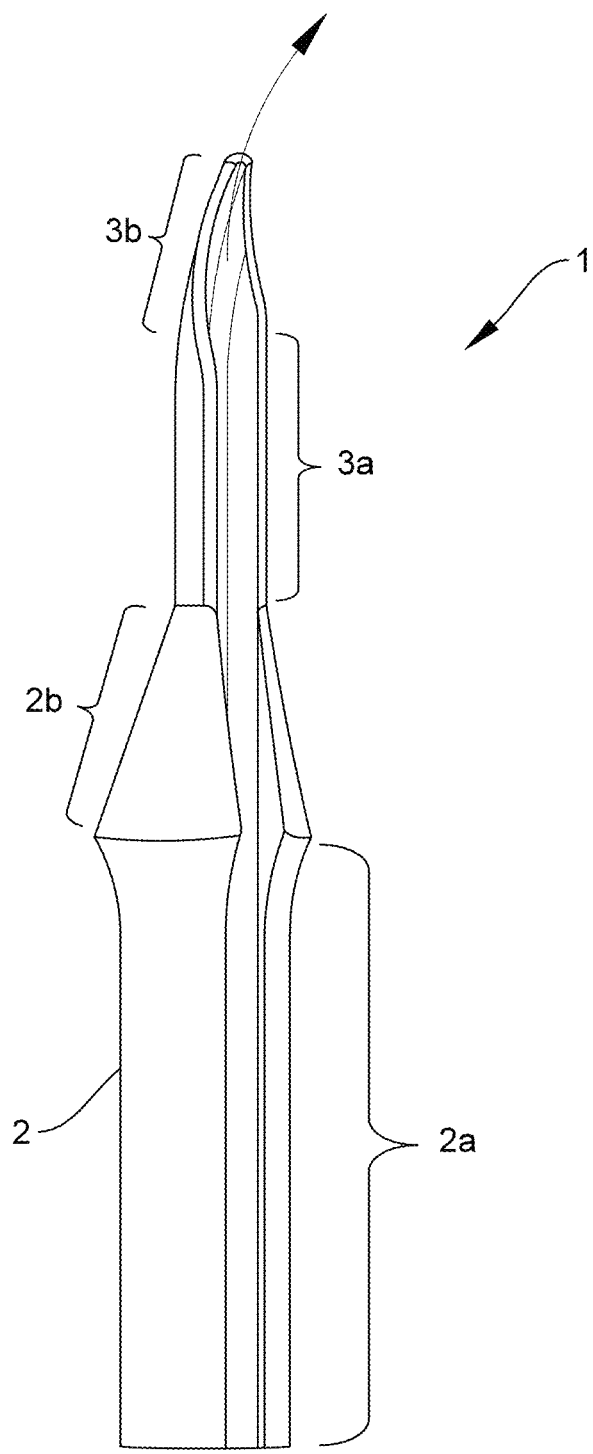
FIG. 9 shows a digital rendering of a thoracostomy device generally from a first front quarter elevation view, in accordance with one embodiment of the invention.

FIG. 9 shows a digital rendering of a thoracostomy device 1 generally from a first front quarter elevation view.

Figure 10:
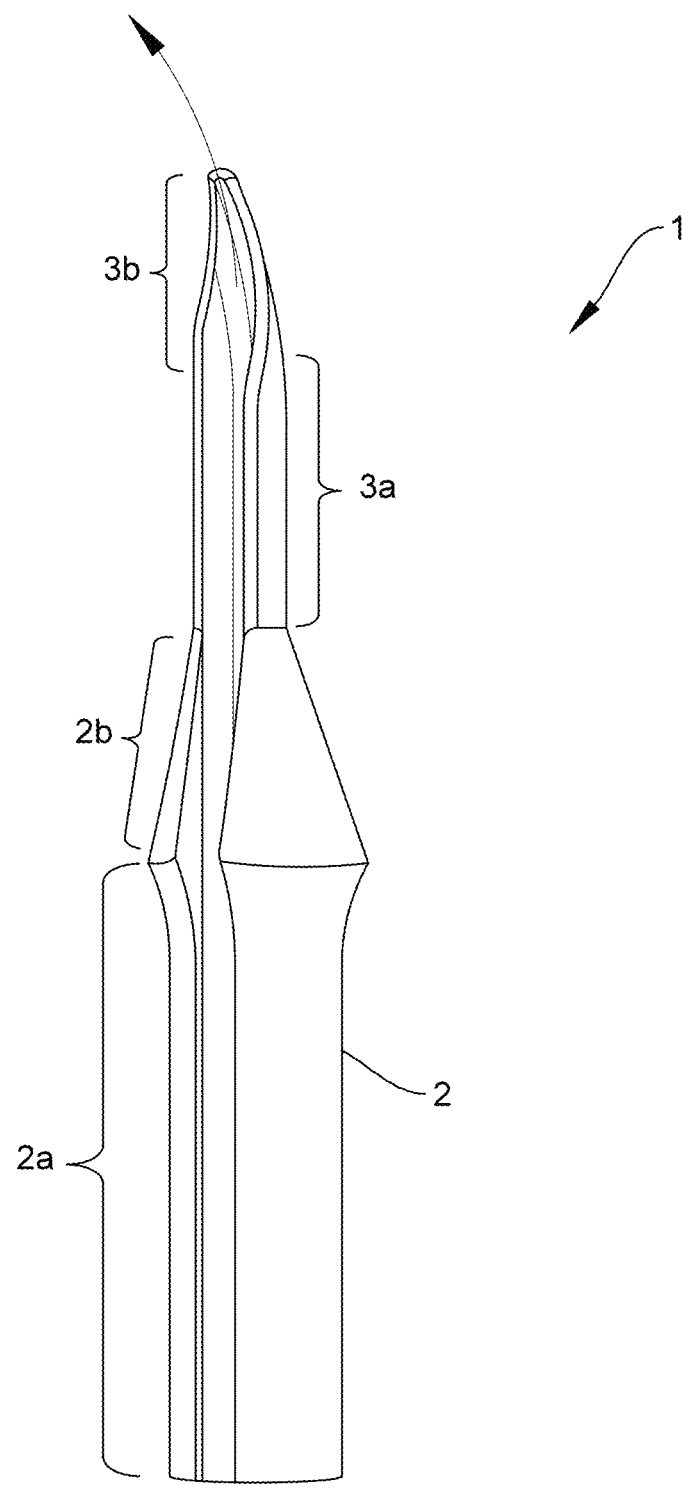
FIG. 10 shows a digital rendering of a thoracostomy device generally from a second front quarter elevation view, in accordance with one embodiment of the invention.

FIG. 10 shows a digital rendering of a thoracostomy device 1 generally from a second front quarter elevation view.

Figure 11:
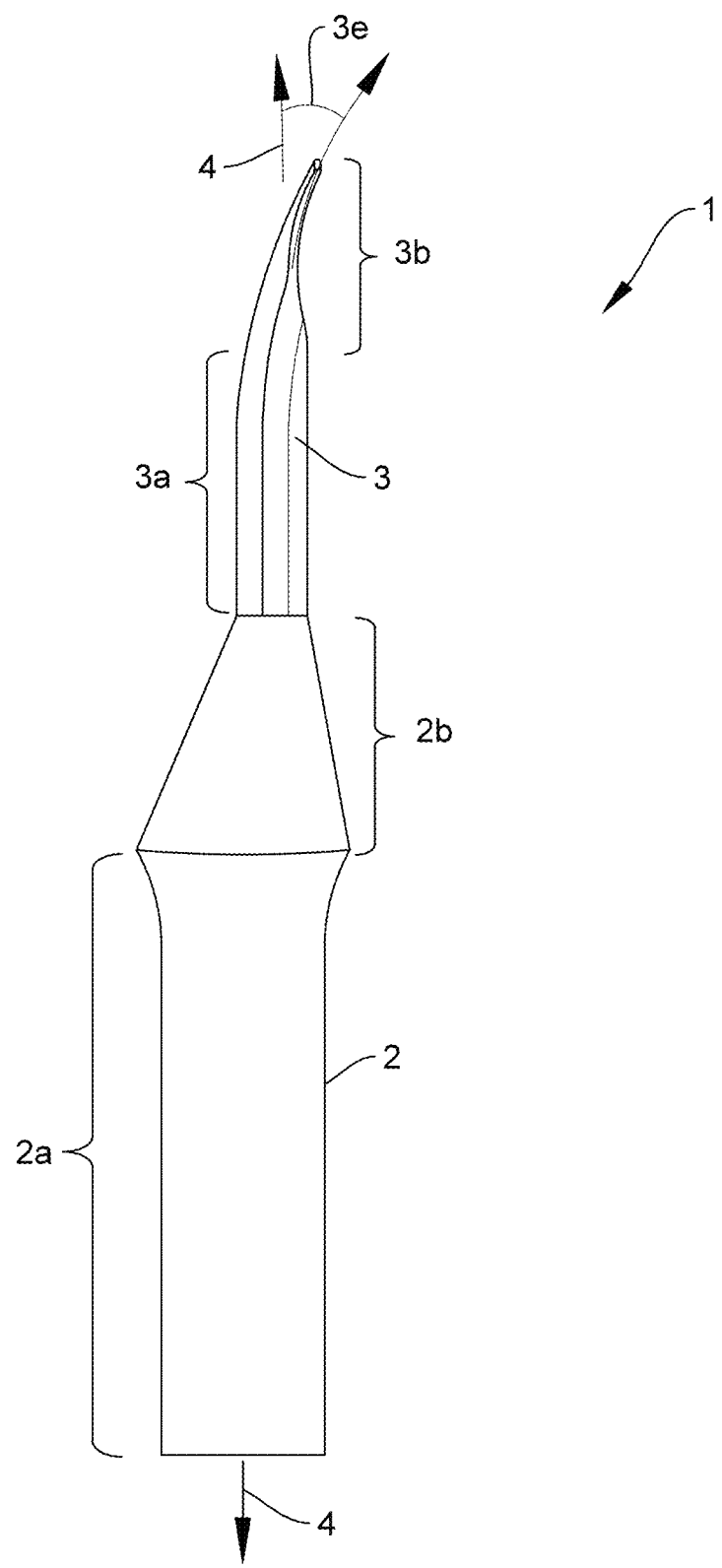
FIG. 11 shows a digital rendering of a thoracostomy device generally from a first lateral elevation view, in accordance with one embodiment of the invention.

FIG. 11 shows a digital rendering of a thoracostomy device 1 generally from a first lateral elevation view.

Figure 12:
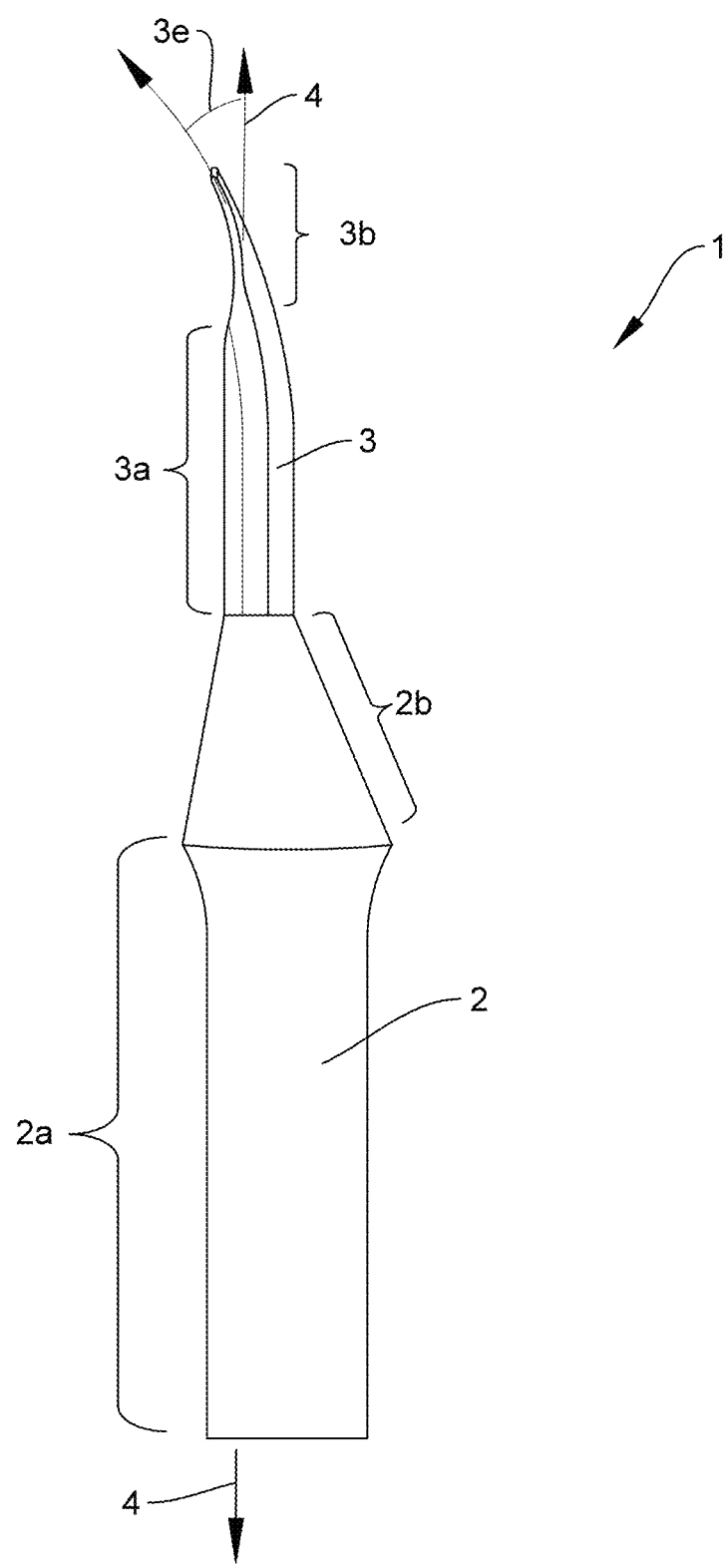
FIG. 12 shows a digital rendering of a thoracostomy device generally from a second lateral elevation view, opposite the first lateral elevation view, in accordance with one embodiment of the invention.

FIG. 12 shows a digital rendering of a thoracostomy device 1 generally from a second lateral elevation view, opposite the first lateral elevation view.

Figure 13:
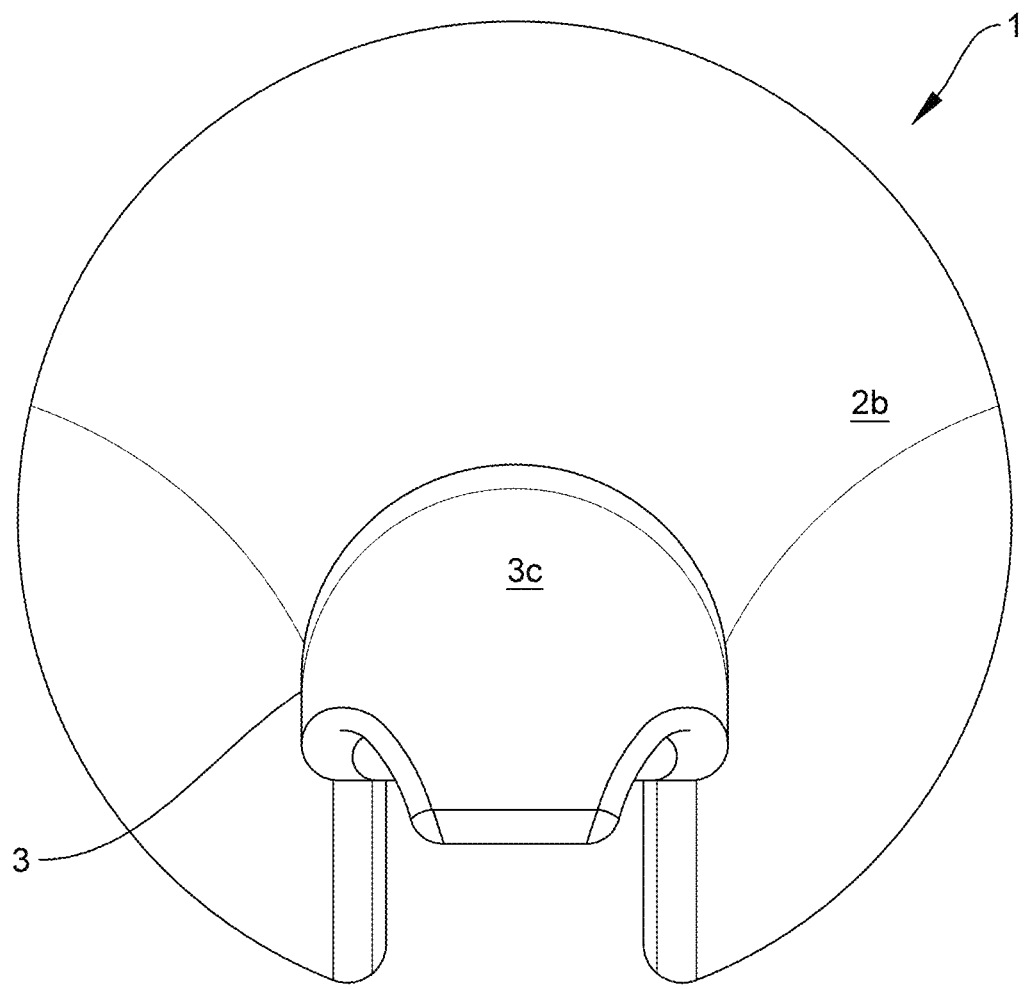
FIG. 13 shows a digital rendering of a thoracostomy device generally from a top slight rear perspective view, in accordance with one embodiment of the invention.

FIG. 13 shows a digital rendering of a thoracostomy device 1 generally from a top slight rear perspective view.

Figure 14:
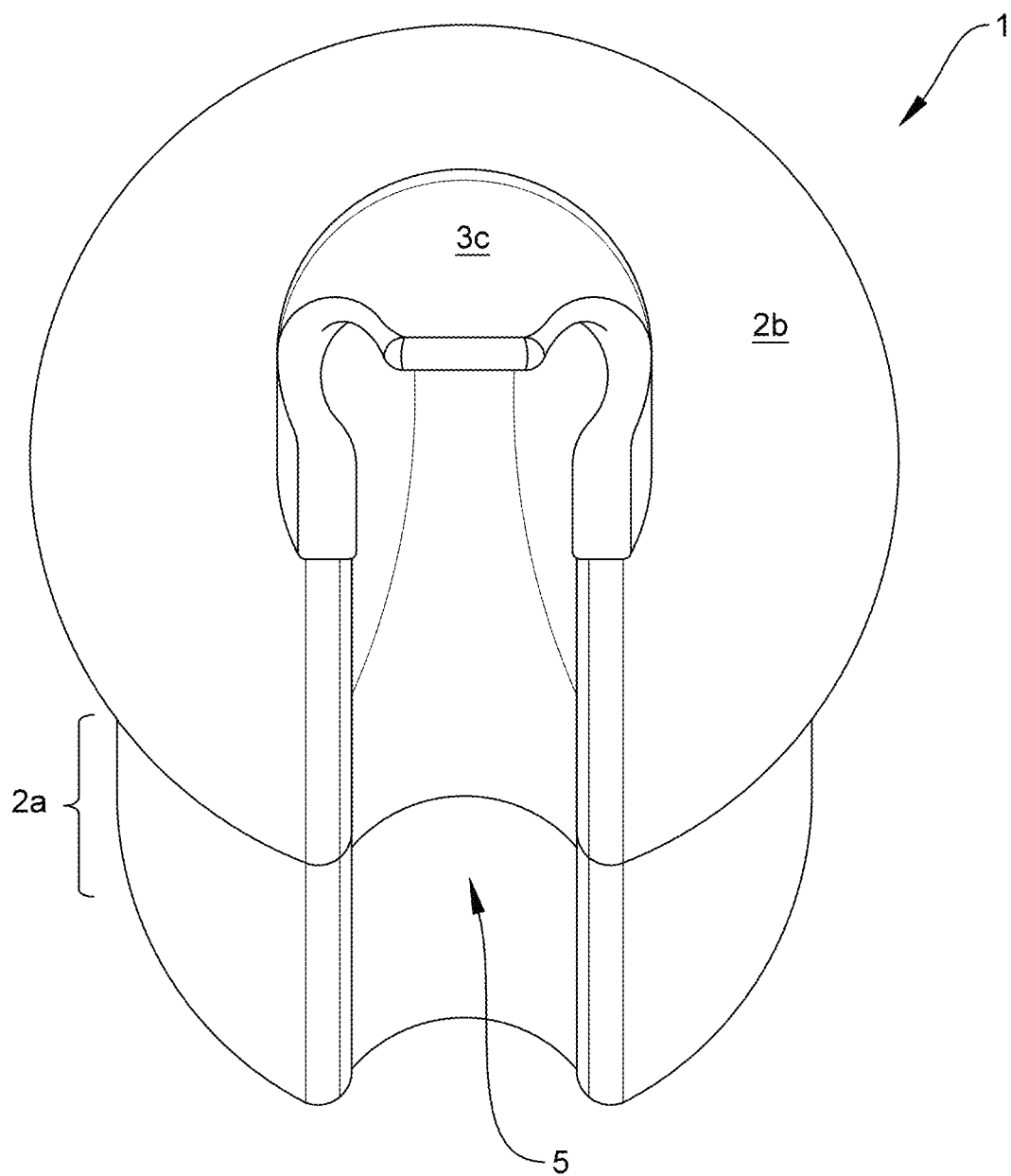
FIG. 14 shows a digital rendering of a thoracostomy device generally from a top slight front perspective view, in accordance with one embodiment of the invention.

FIG. 14 shows a digital rendering of a thoracostomy device 1 generally from a top slight front perspective view.

Figure 15:
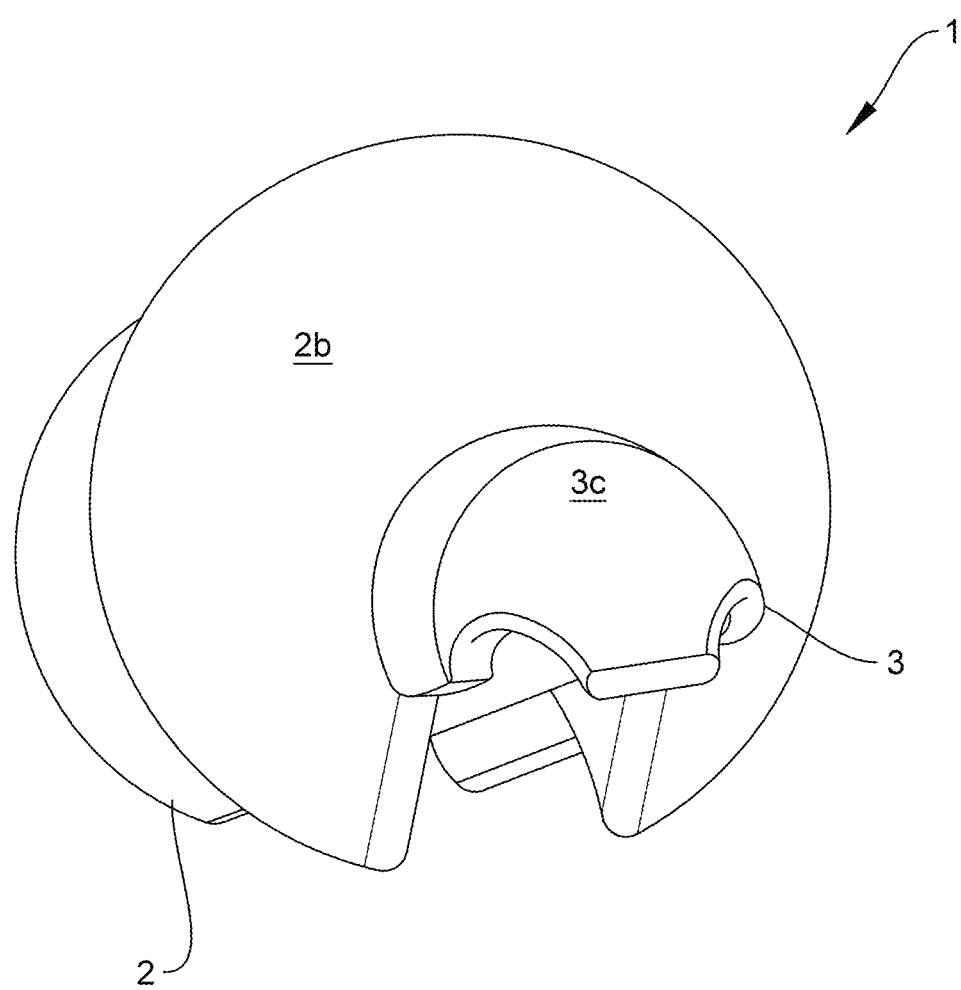
FIG. 15 shows a digital rendering of a thoracostomy device generally from a top slight front quarter perspective view, in accordance with one embodiment of the invention.

FIG. 15 shows a digital rendering of a thoracostomy device 1 generally from a top slight front quarter perspective view.

Figure 16:
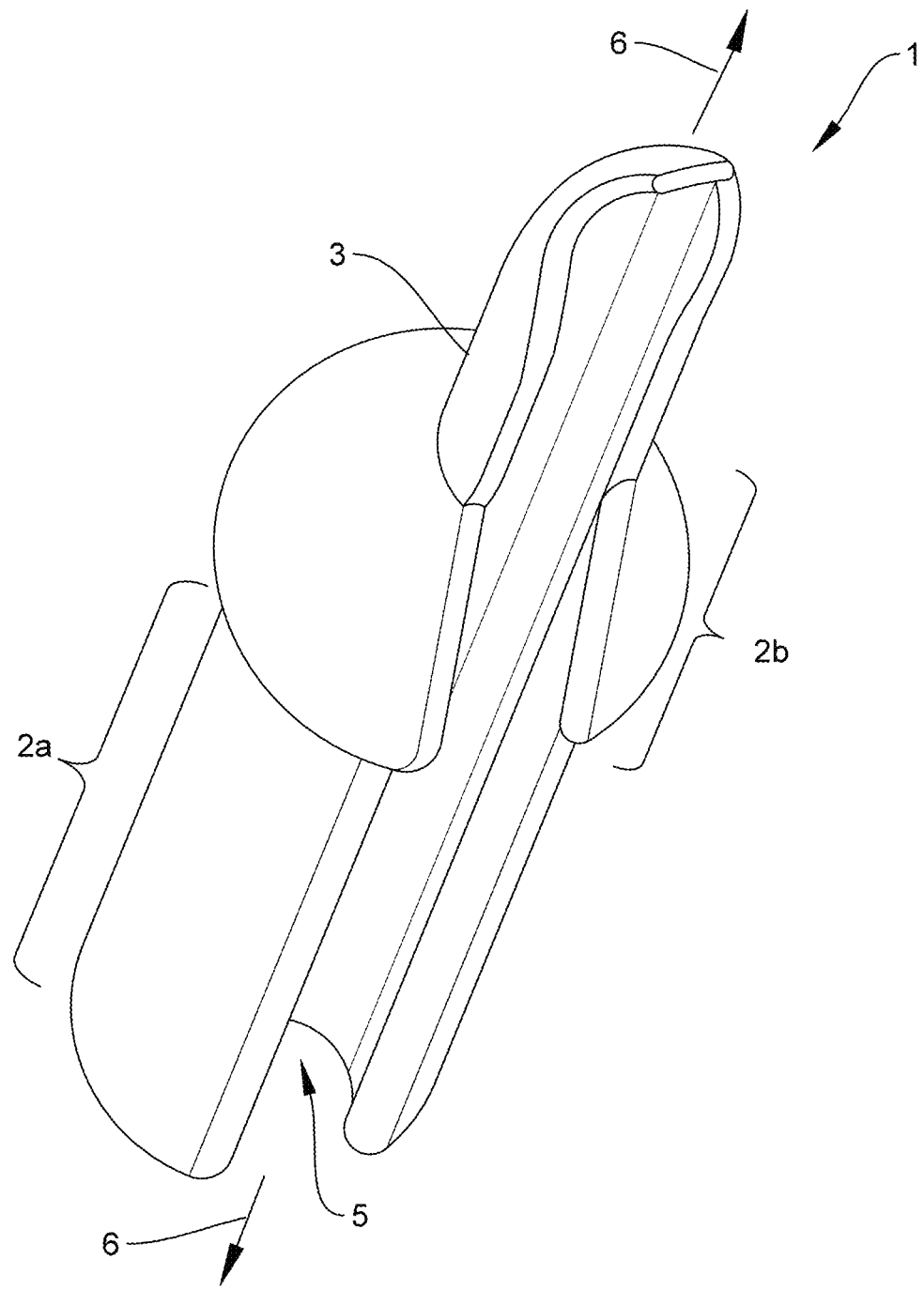
FIG. 16 shows a digital rendering of a thoracostomy device generally from a top front quarter perspective view, in accordance with one embodiment of the invention.

FIG. 16 shows a digital rendering of a thoracostomy device 1 generally from a top front quarter perspective view.

Figure 17:
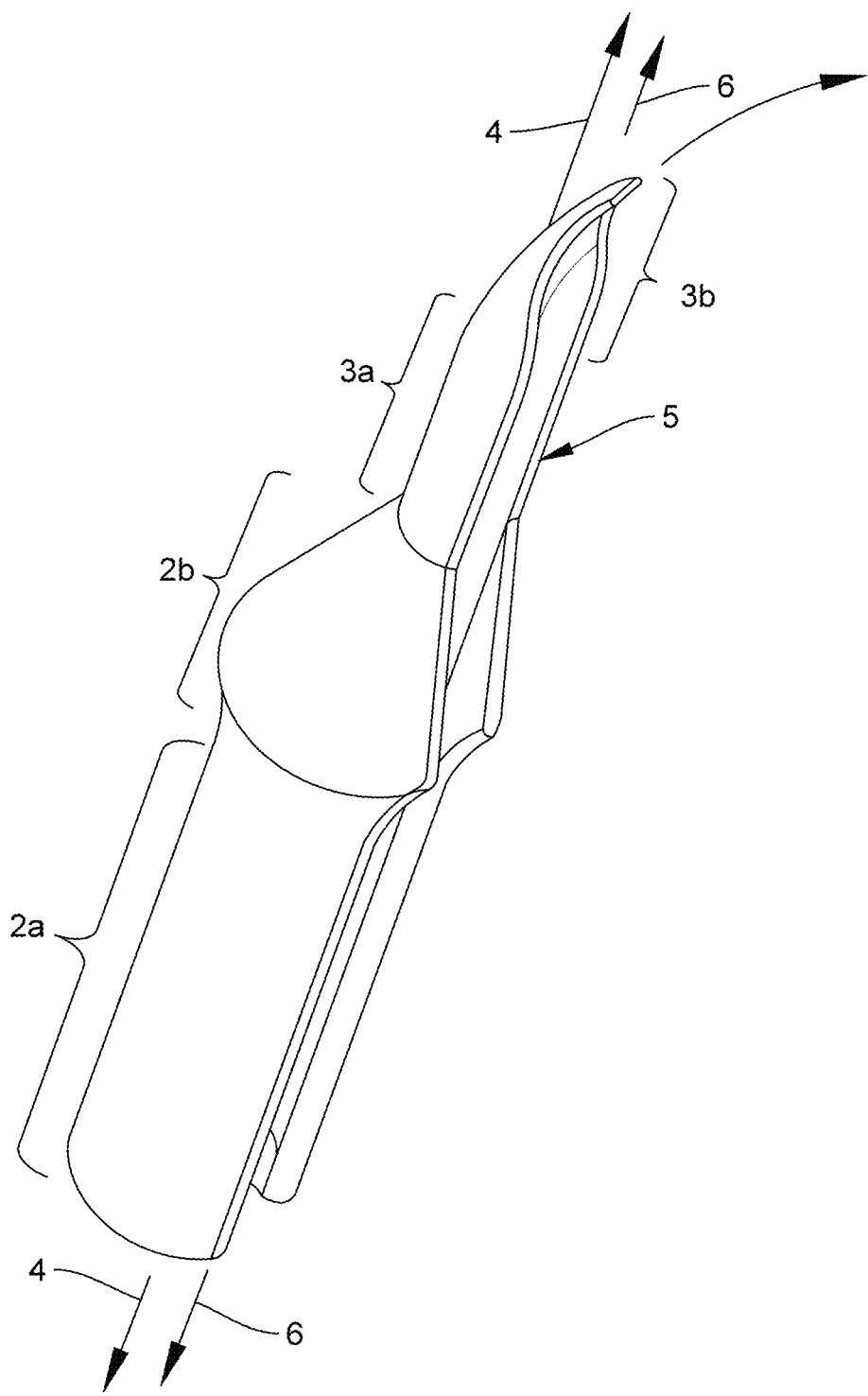
FIG. 17 shows a digital rendering of a thoracostomy device generally from a first lateral front quarter perspective view, in accordance with one embodiment of the invention.

FIG. 17 shows a digital rendering of a thoracostomy device 1 generally from a first lateral front quarter perspective view.

Figure 18:
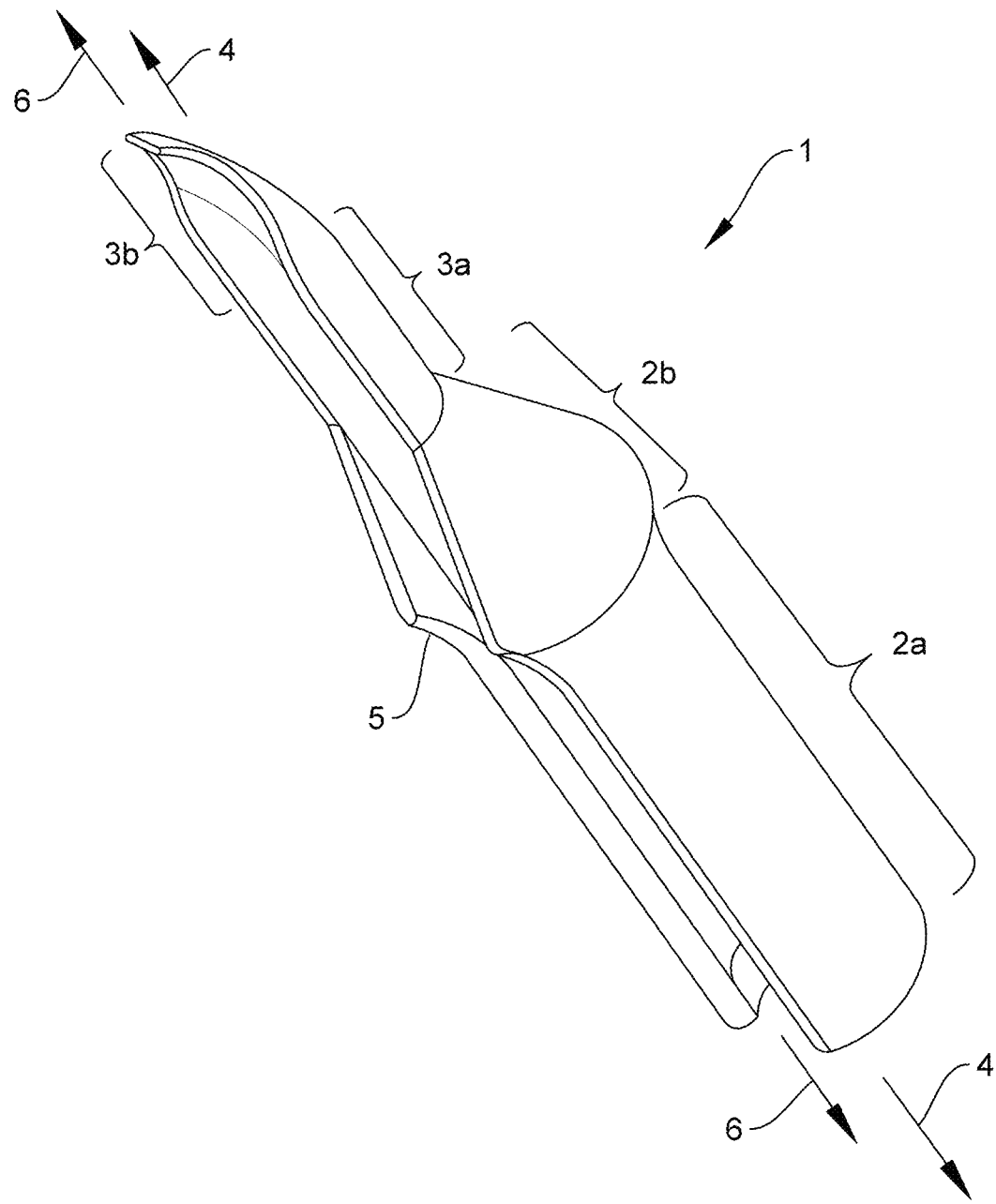
FIG. 18 shows a digital rendering of a thoracostomy device generally from a second lateral front quarter perspective view, in accordance with one embodiment of the invention.

FIG. 18 shows a digital rendering of a thoracostomy device 1 generally from a second lateral front quarter perspective view.

In one embodiment as shown in the foregoing Figures, the width of the handle portion 2 is greater than the width of the insertion portion 3.

In one embodiment as shown in the foregoing Figures, the handle portion 2 comprises a main portion 2a and a relatively minor distally tapered portion 2b, tapered toward the insertion portion 3.

In one embodiment as shown in the foregoing Figures, the relatively minor distally tapered portion 2b comprises an offset frustoconical shape.

In one embodiment as shown in the foregoing Figures, the surface of the relatively minor distally tapered portion 2b is continuous with the second outer lateral surface 3a.

In one embodiment as shown in the above-described Figures, the insertion portion forms a channel 5 having an internal cross-section defining an arc 7 of from about 210 degrees to about 325 degrees, and, more narrowly, defining an arc 7 of from about 250 degrees to about 290 degrees.

In one embodiment as shown by example in the foregoing Figures, the linear portion 3a is relatively greater in length than the curved terminal portion 3b.

In one embodiment as shown by example in the foregoing Figures, the linear portion 3a is tapered toward the curved terminal portion 3b.

In one embodiment as shown by example in the foregoing Figures, the linear portion 3a having a longitudinal axis, wherein the curved terminal portion 3b is sufficiently curved so as to provide a defection angle (angle 3e) of its terminal end from about 5 degrees to about 35 degrees from the longitudinal axis 4 of the linear portion 3a; and, more narrowly, from about 10 degrees to about 30 degrees from the longitudinal axis of the linear portion, and most preferably about 17.5 degrees.

Another embodiment of the present invention is shown in FIGS. 19 through 33 wherein like numerals refer to the same portions and features.

Figure 19:
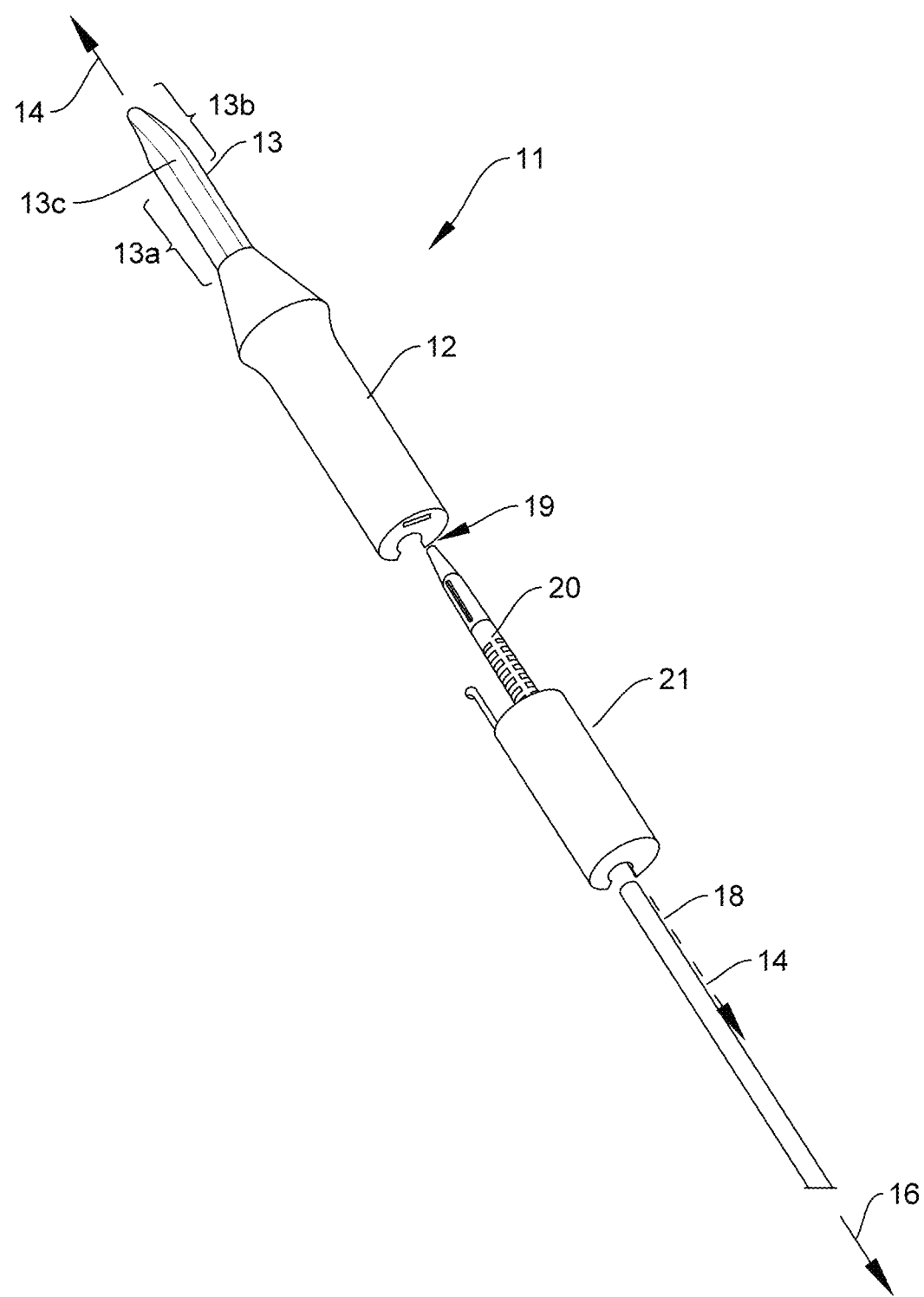
FIG. 19 shows a digital rendering of a thoracostomy device showing an exploded view from a lateral rear quarter perspective view, and showing an enclosed scalpel and guided chest tube, in accordance with another embodiment of the invention.

FIG. 19 shows a digital rendering of a thoracostomy device 1 showing an exploded view from a lateral rear quarter perspective view, and showing an enclosed scalpel and guided chest tube, in accordance with another embodiment of the invention.

FIG. 19 shows thoracostomy device 11 adapted to be extended into an incision in a patient, comprising a handle portion 12, an insertion portion 13 extending from the handle portion 12, and having a linear portion 13a and a curved terminal portion 13b, the insertion portion 13b having opposed substantially continuous first inner 13d and second outer 13c lateral surfaces, the device defining a central axis 14 extending therethrough, and a continuous channel 15 extending through the handle portion 12 and insertion portion 13 and open to the first inner lateral surface 13d, the channel 15 having a medial axis 16 offset from and parallel to the central axis 14, the channel 15 adapted to guide a tube 18 along the medial axis 16 while being adapted to allow a tube to be removed laterally of the channel 15; and the handle portion 12 having a compartment 19 adapted to contain a scalpel 20.

The thoracostomy device 11 may also have a handle portion 12 additionally comprises a releasable container portion 21 adapted to contain a flexible tube. Releasable container 21 may be held onto handle portion 12 by a clasp 22 (that engages slot 22a) or similar means, such as an interference fit, threaded attachment, opposed pins and holes, etc.

The thoracostomy device 11 may optionally be provided with releasable container 21 that may contain a flexible tube 18.

In one embodiment of the present invention the thoracostomy device 11 may include a light source, such as a distally directed light source, such as may be incorporated into handle portion 12 that may be constructed to incorporate a light source 23 (such as providing a switchable battery-operated light within a modeled aperture of the handle portion 12) directed distally toward the curved terminal portion 13b. In another embodiment, the thoracostomy device 11 may include a light source incorporated into the device such that the light is directed from the channel's inner surface 15a and directed toward the curved terminal portion 13b.

Figure 20:
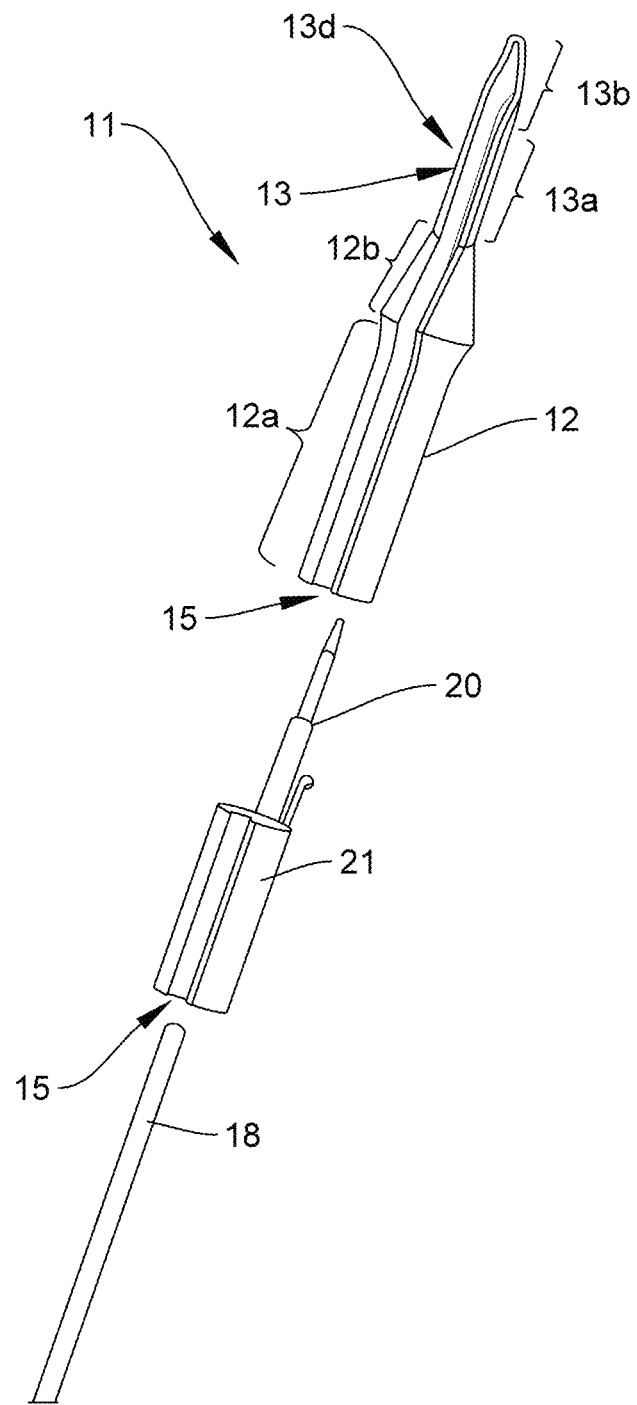
FIG. 20 shows a digital rendering of a thoracostomy device showing an exploded view from a lateral front quarter perspective view, and showing an enclosed scalpel and guided chest tube, in accordance with another embodiment of the invention.

FIG. 20 shows a digital rendering of a thoracostomy device 11 showing an exploded view from a lateral front quarter perspective view, and showing an enclosed scalpel 20 and guided chest tube 18.

Figure 21:
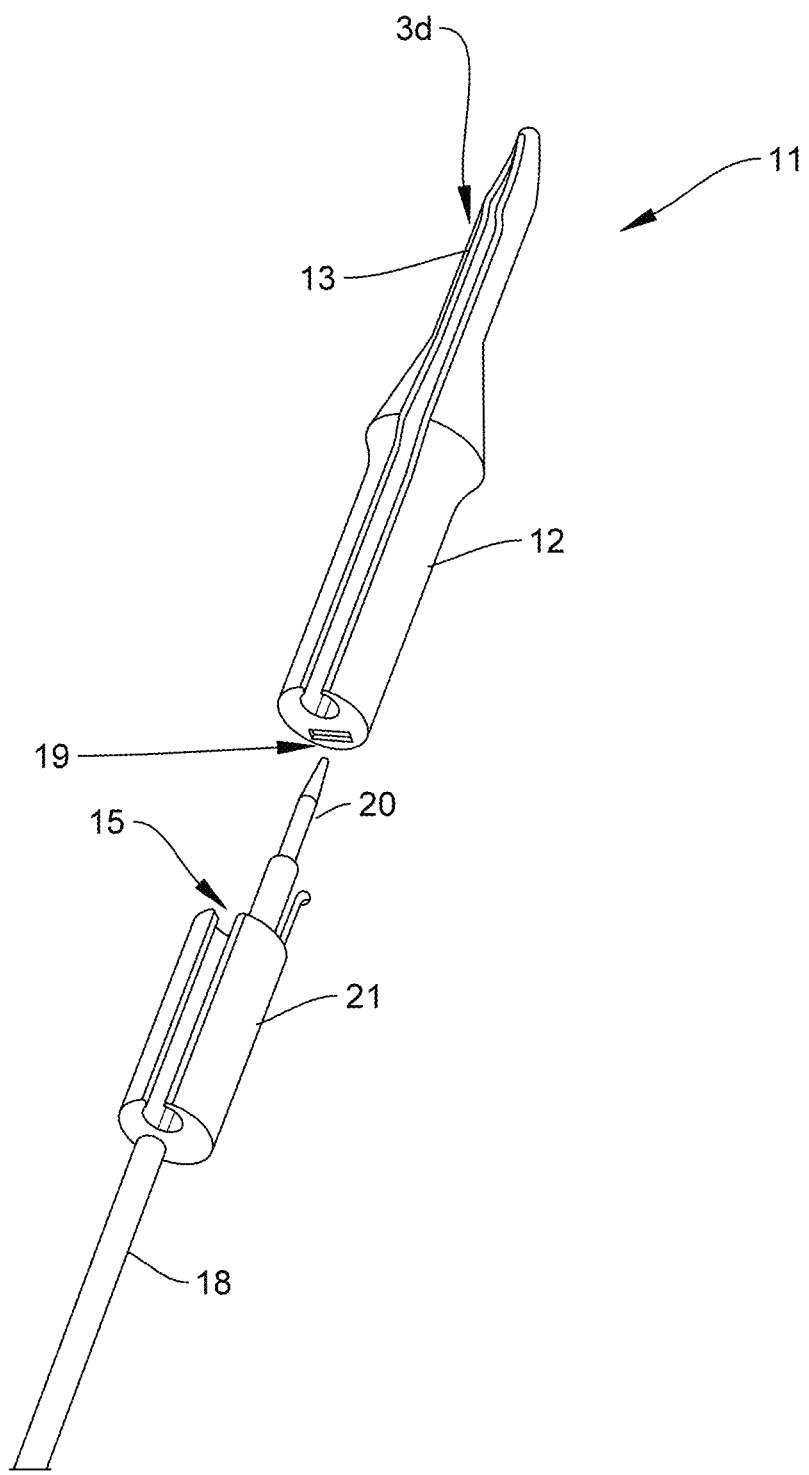
FIG. 21 shows a digital rendering of a thoracostomy device showing an exploded view from a lower front quarter perspective view, and showing an enclosed scalpel and guided chest tube, in accordance with another embodiment of the invention.

FIG. 21 shows a digital rendering of a thoracostomy device 11 showing an exploded view from a lower front quarter perspective view, and showing an enclosed scalpel 20 and guided chest tube 18.

Figure 22:
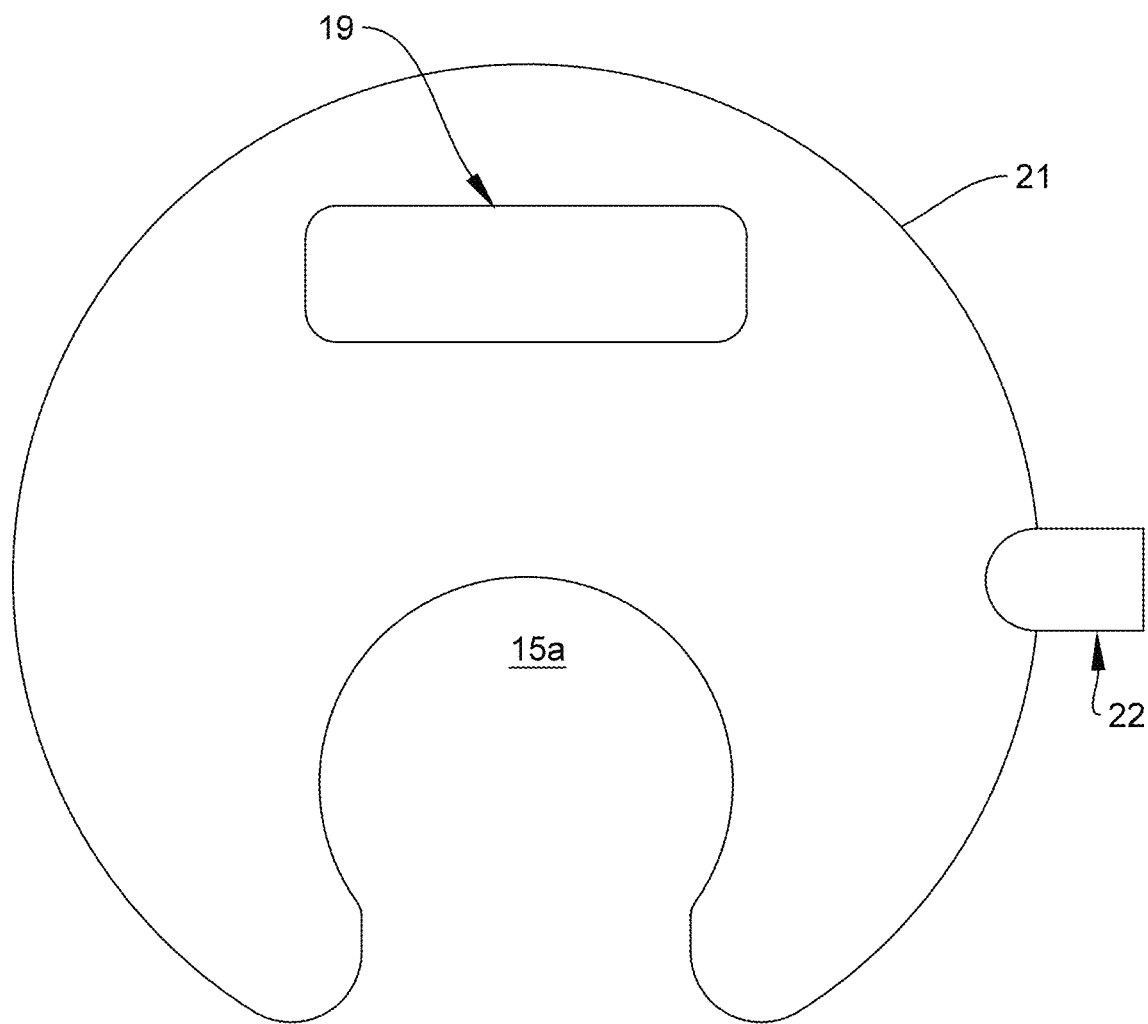
FIG. 22 shows a digital rendering of the handle portion of a thoracostomy device generally from a bottom plan view, in accordance another embodiment of the invention.

FIG. 22 shows a digital rendering of the handle portion of a thoracostomy device 11 generally from a bottom plan view, and showing channel 15 inner surface 15a, the compartment 19 formed by the referenced aperture in the distal portion of container portion 21 and/or a counterpart aperture (19a) in the proximal end of handle portion 12, and clasp 22.

Figure 23:
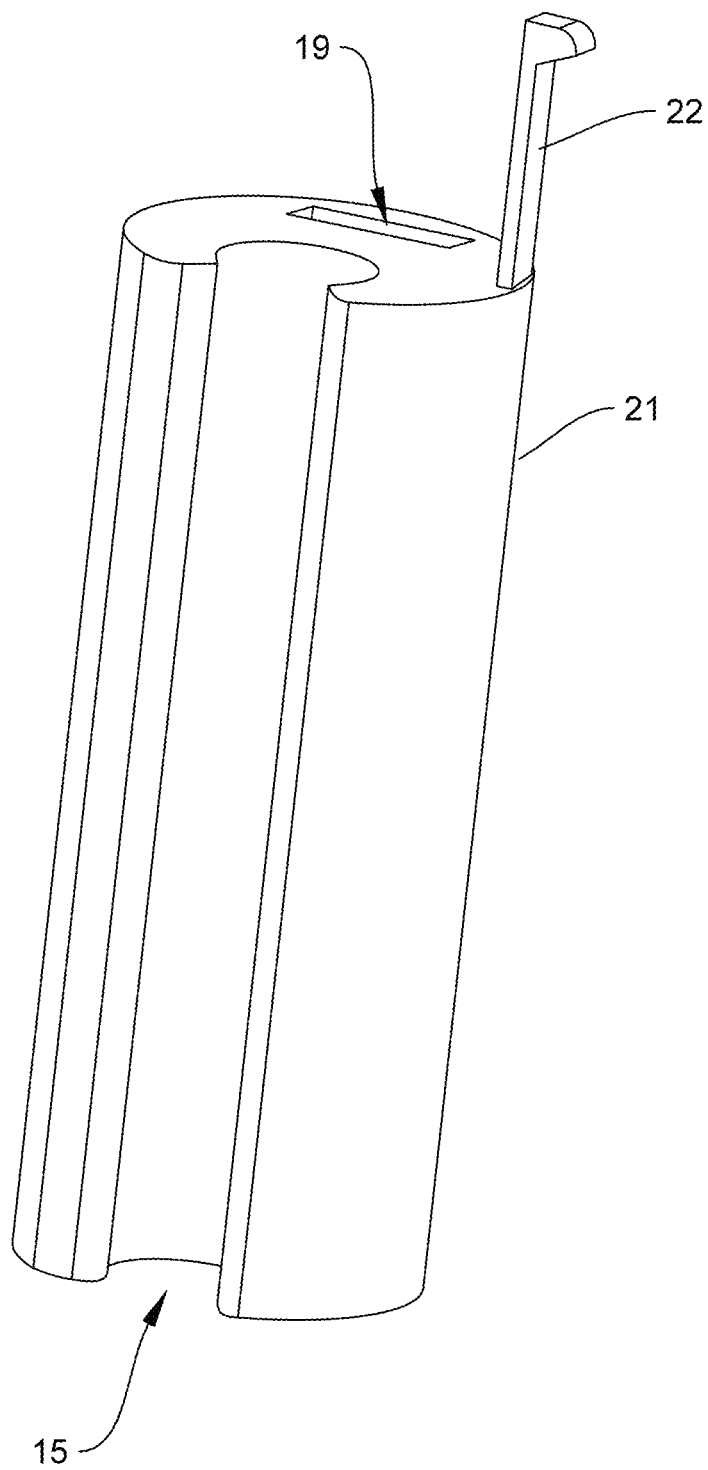
FIG. 23 shows a digital rendering of the handle portion of a thoracostomy device generally from a front perspective view, in accordance another embodiment of the invention.

FIG. 23 shows a digital rendering of the releasable container portion 21 of a thoracostomy device 11 generally from a front perspective view.

Figure 24:
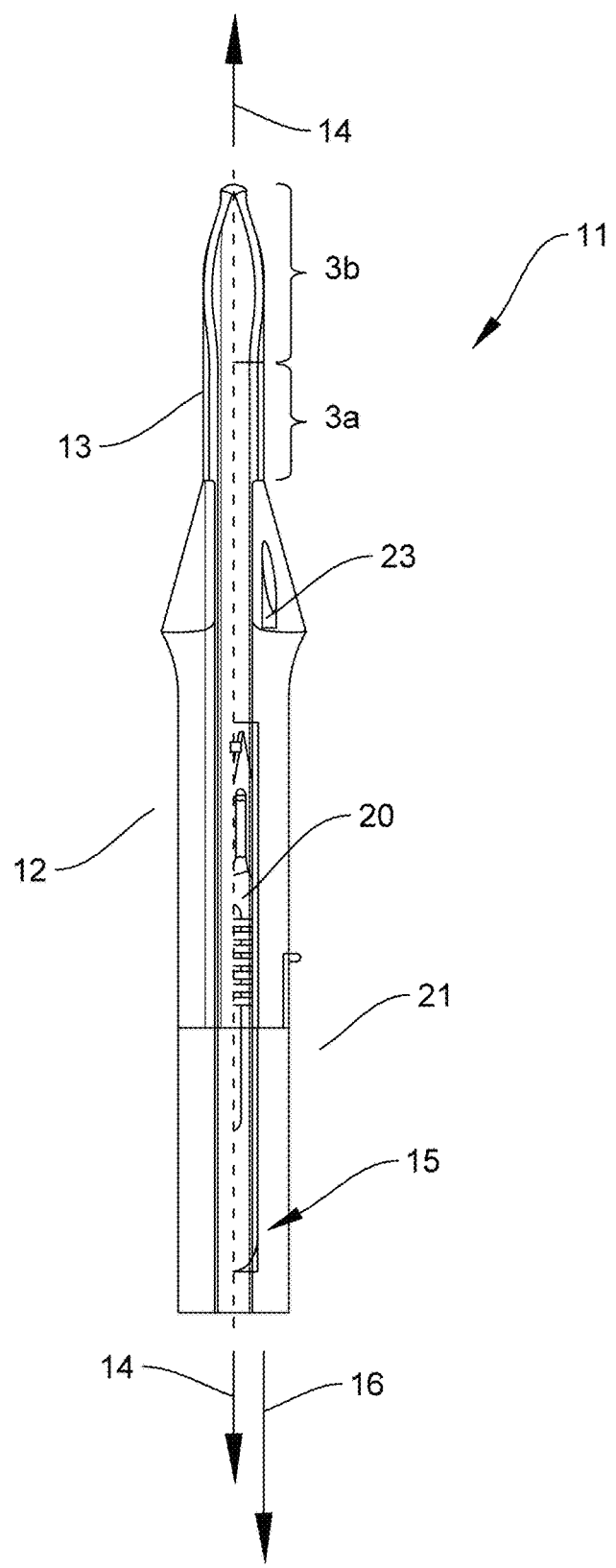
FIG. 24 shows a digital rendering of a thoracostomy device showing a partially sectioned view from a front elevation view, and showing an enclosed scalpel and channel for a chest tube, in accordance with another embodiment of the invention.

FIG. 24 shows a digital rendering of a thoracostomy device 11 showing a partially sectioned view from a front elevation view, and showing an enclosed scalpel 20 and channel 15 for a chest tube 18. FIG. 24 also shows container portion 21 which together with a counterpart aperture in the proximal end of handle portion 12, contains scalpel 20.

Figure 25:
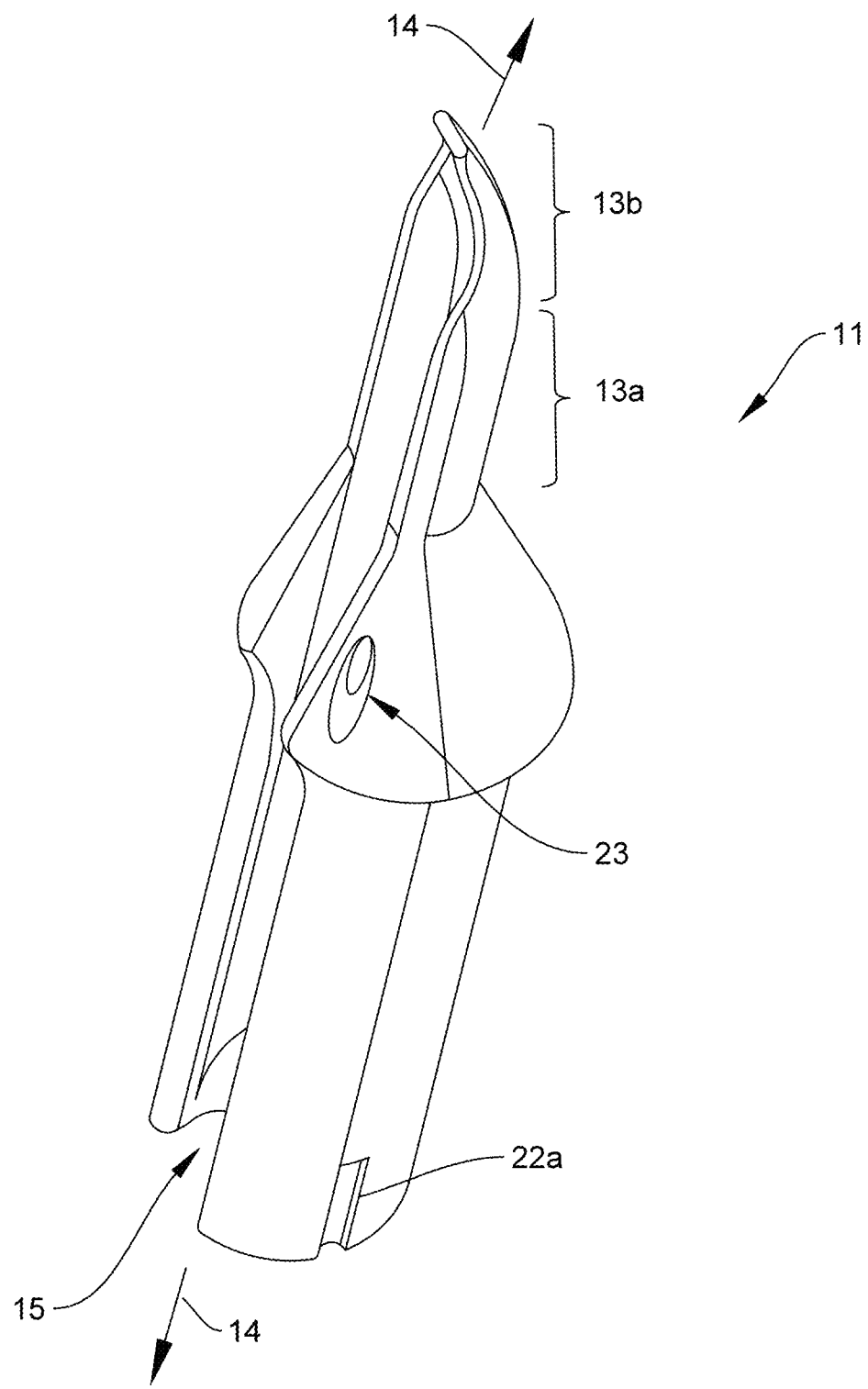
FIG. 25 shows a digital rendering of a thoracostomy device generally from a top front quarter perspective view, in accordance with another embodiment of the invention.

FIG. 25 shows a digital rendering of a thoracostomy device 11 generally from a top front quarter perspective view. This view shows handle portion 12 that may be constructed to incorporate a light source 23, and the slot 22a positioned to be engaged by clasp 22.

Figure 26:
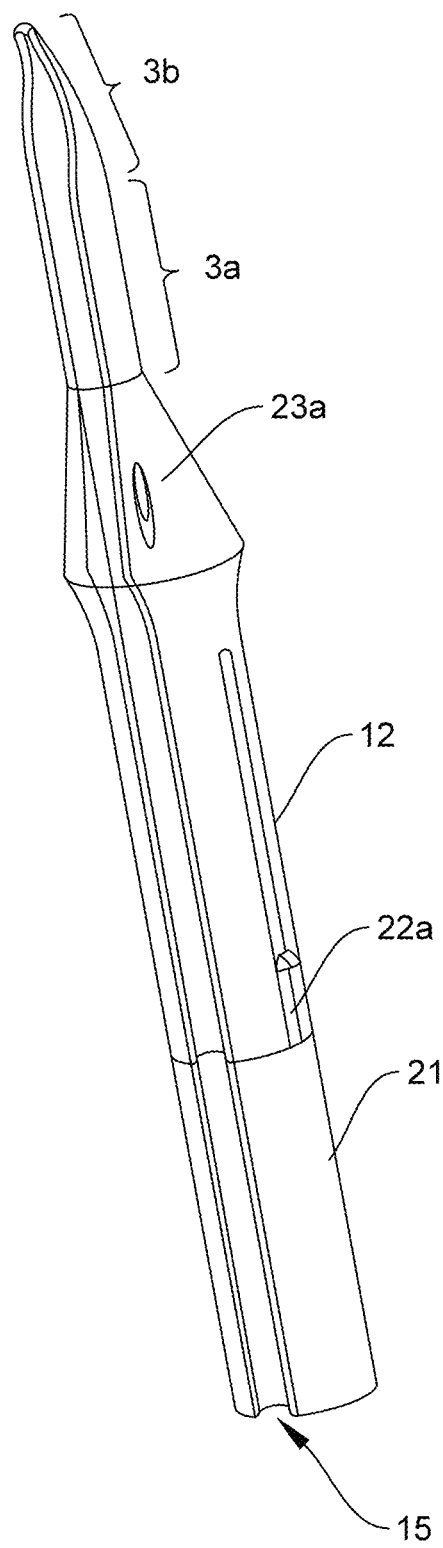
FIG. 26 shows a digital rendering of a thoracostomy device generally from a front perspective view, with a removable extension of the handle portion thereof to enclose a scalpel, in accordance another embodiment of the invention.

FIG. 26 shows a digital rendering of a thoracostomy device 11 generally from a front perspective view, with a removable extension of the handle portion 12 (such as container portion 21) to enclose a scalpel 20.

Figure 27:
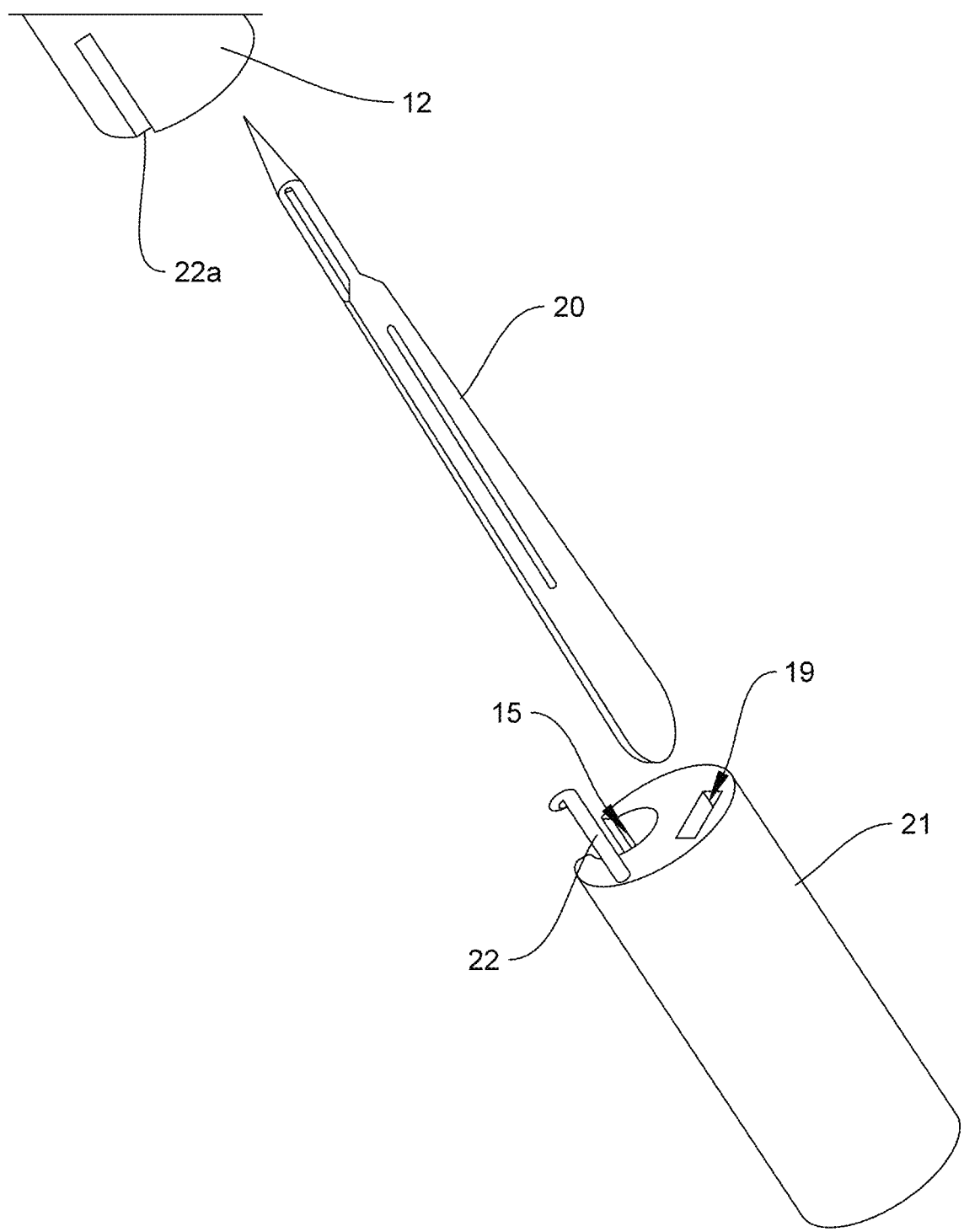
FIG. 27 shows a digital rendering of a thoracostomy device showing an exploded view from a lateral upper quarter perspective view, and showing an enclosed scalpel being deployed, in accordance with another embodiment of the invention.

FIG. 27 shows a digital rendering of a thoracostomy device 11 showing an exploded view from a lateral upper quarter perspective view, and showing an enclosed scalpel 20 being deployed by the longitudinal separation of the container portion 21 from the counterpart handle portion 12.

Figure 28:
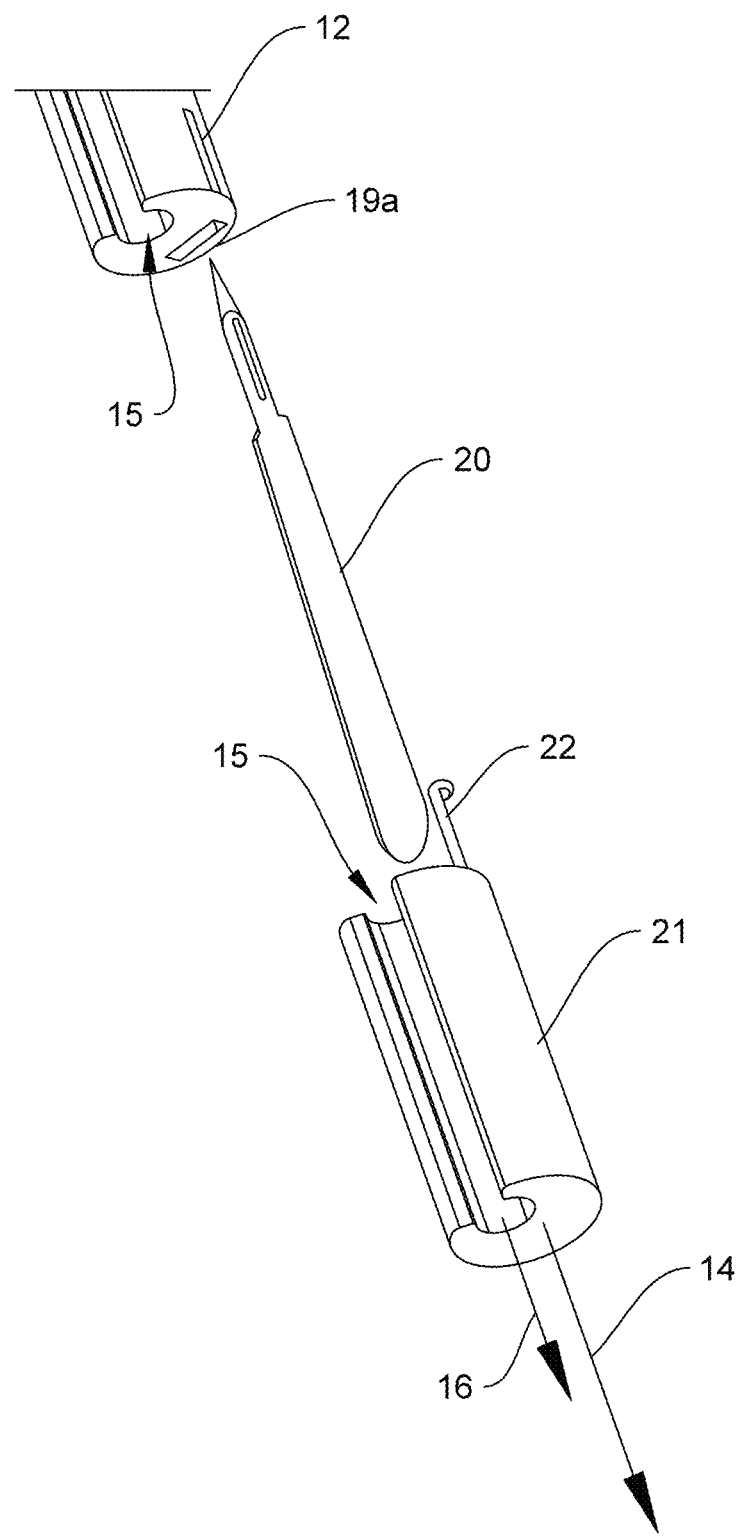
FIG. 28 shows a digital rendering of a thoracostomy device showing an exploded view from a lateral lower quarter perspective view, and showing an enclosed scalpel being deployed, in accordance with another embodiment of the invention.

FIG. 28 shows a digital rendering of a thoracostomy device 11 showing an exploded view from a lateral lower quarter perspective view, and showing container portion 21 which together with a counterpart aperture in the proximal end of handle portion 12 forms a contained space and an enclosed scalpel 20.

Figure 29:
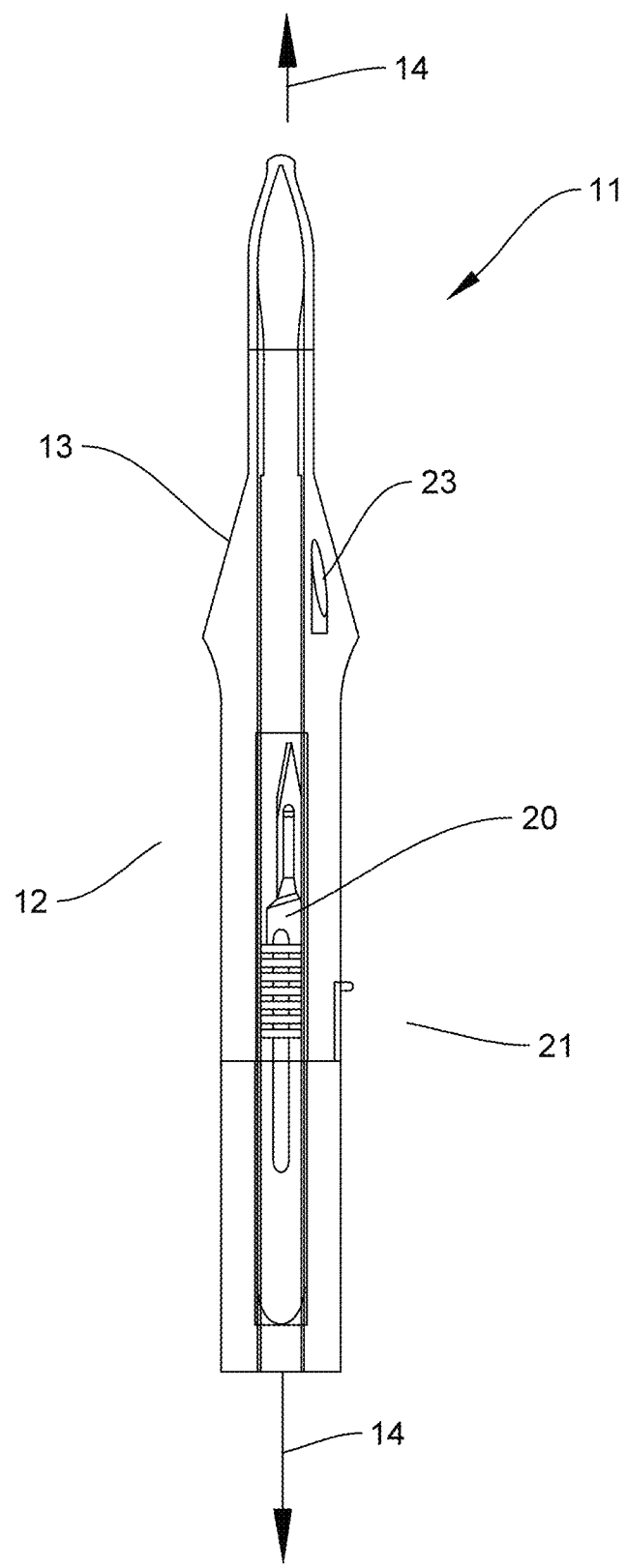
FIG. 29 shows a digital rendering of a thoracostomy device showing a partially sectioned view from a front elevation view, and showing an enclosed scalpel, in accordance with another embodiment of the invention.

FIG. 29 shows a digital rendering of a thoracostomy device 11 showing a partially sectioned view from a front elevation view, and showing an enclosed scalpel 20 in the enclosed container space formed by apertures 19 and 19a.

Figure 30:
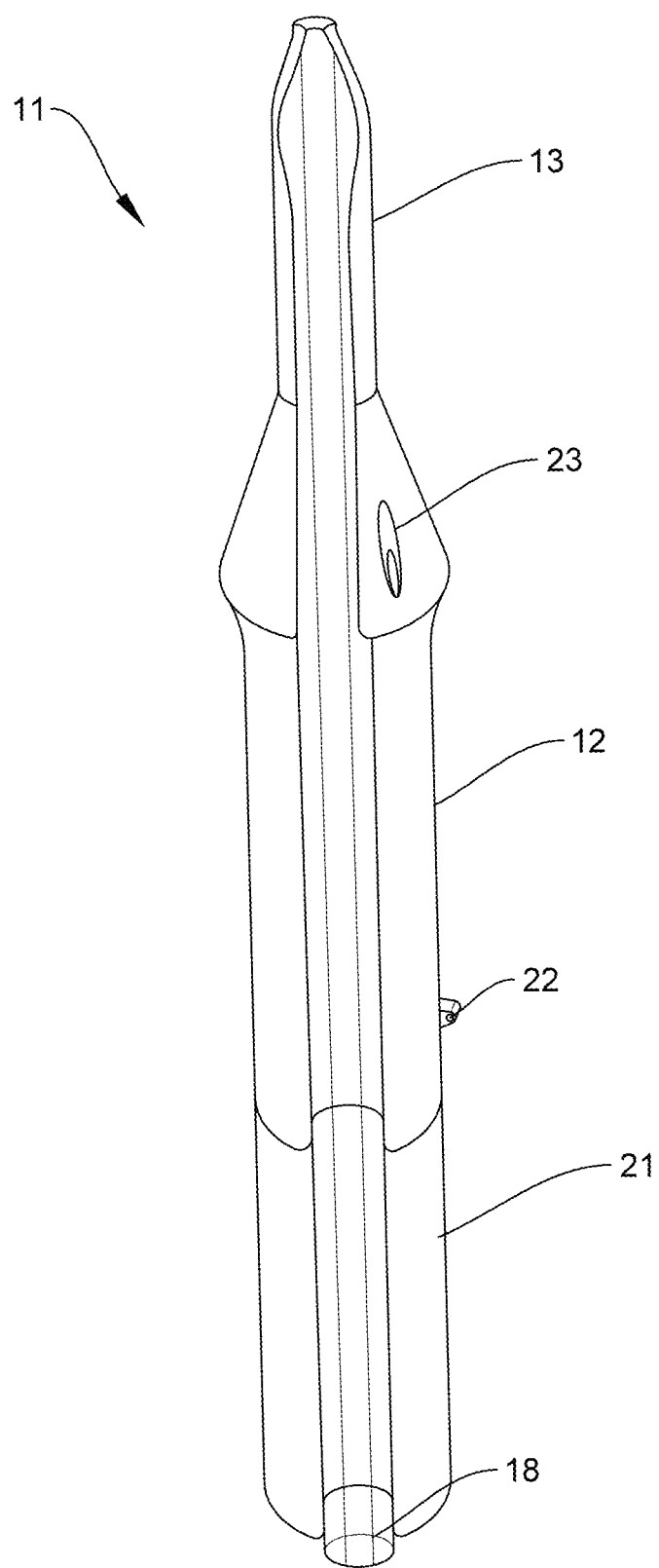
FIG. 30 shows a digital rendering of a thoracostomy device generally from a front upper perspective view, with a removable extension of the handle portion thereof to enclose a scalpel, in accordance with another embodiment of the invention.

FIG. 30 shows a digital rendering of a thoracostomy device 11 generally from a front upper perspective view, with a removable extension of the handle portion 12 thereof to enclose a scalpel 20, and shown guiding chest tube 18.

Figure 31:
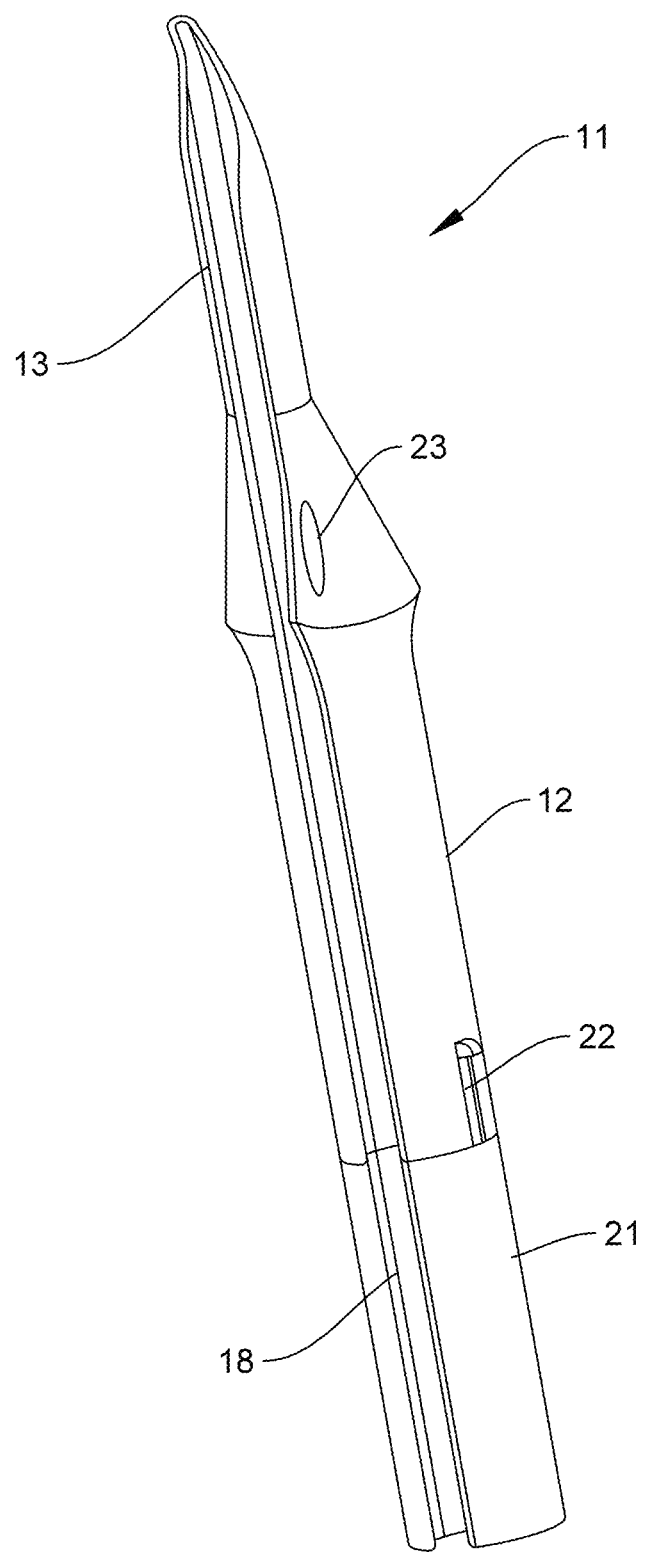
FIG. 31 shows a digital rendering of a thoracostomy device generally from a front lateral perspective view, with a removable extension of the handle portion thereof to enclose a scalpel, in accordance another embodiment of the invention.

FIG. 31 shows a digital rendering of a thoracostomy device 11 generally from a front lateral perspective view, with a removable extension of the handle portion 12 thereof to enclose a scalpel 20, and shown guiding chest tube 18.

Figure 32:
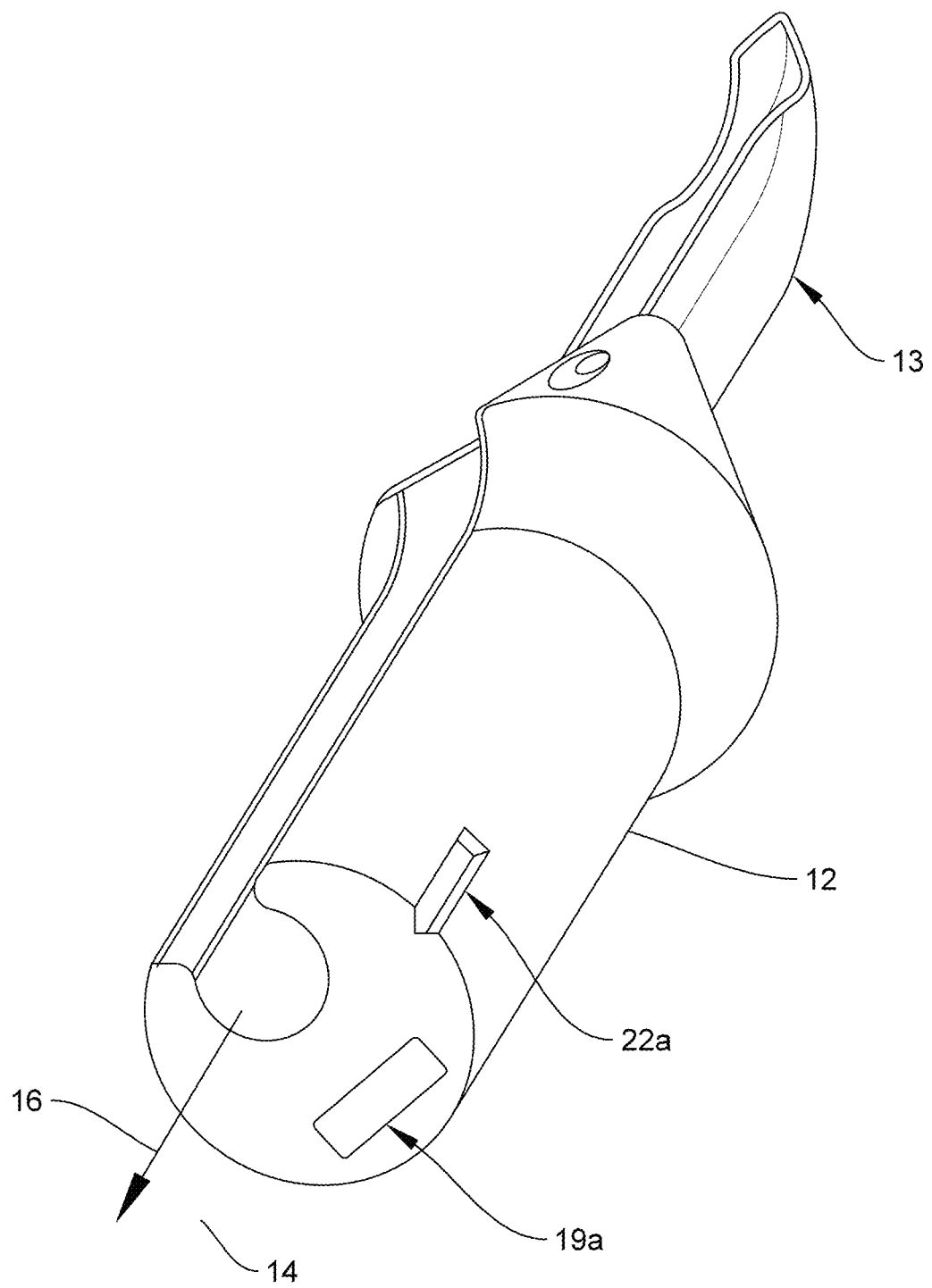
FIG. 32 shows a digital rendering of a thoracostomy device generally from a front lower quarter perspective view, with the removable extension of the handle portion thereof removed to show the compartment that may enclose a scalpel, in accordance another embodiment of the invention.

FIG. 32 shows a digital rendering of a thoracostomy device 1 generally from a front lower quarter perspective view, with the removable extension of the handle portion thereof removed to show the compartment that may enclose a scalpel 20, channel 15 having a medial axis 16 offset from and parallel to the central axis 14, the channel 15 adapted to guide a tube 18 along the medial axis 16 while being adapted to allow a tube to be removed laterally of the channel 15; and the handle portion 12 having a compartment 19 adapted to contain a scalpel 20.

Figure 33:
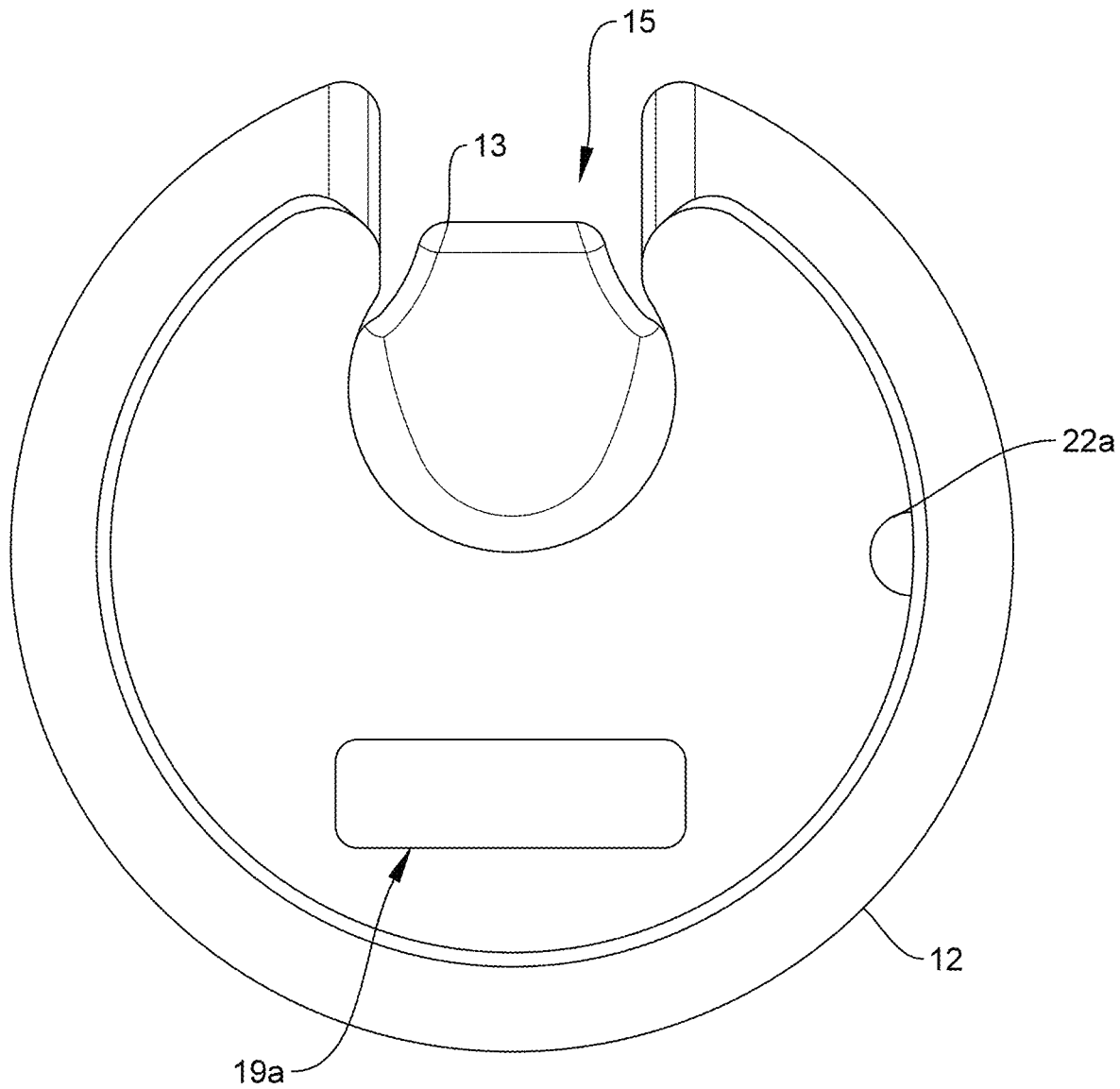
FIG. 33 shows a digital rendering of a thoracostomy device generally from a bottom plan view, with the removable extension of the handle portion thereof removed to show the compartment that may enclose a scalpel, in accordance another embodiment of the invention.

FIG. 33 shows a digital rendering of a thoracostomy device 11 generally from a bottom plan view, with the removable extension of the handle portion 12 thereof removed to show the compartment 19a that may enclose a scalpel or other medical instrument, in accordance another embodiment of the invention.

Figure 34:
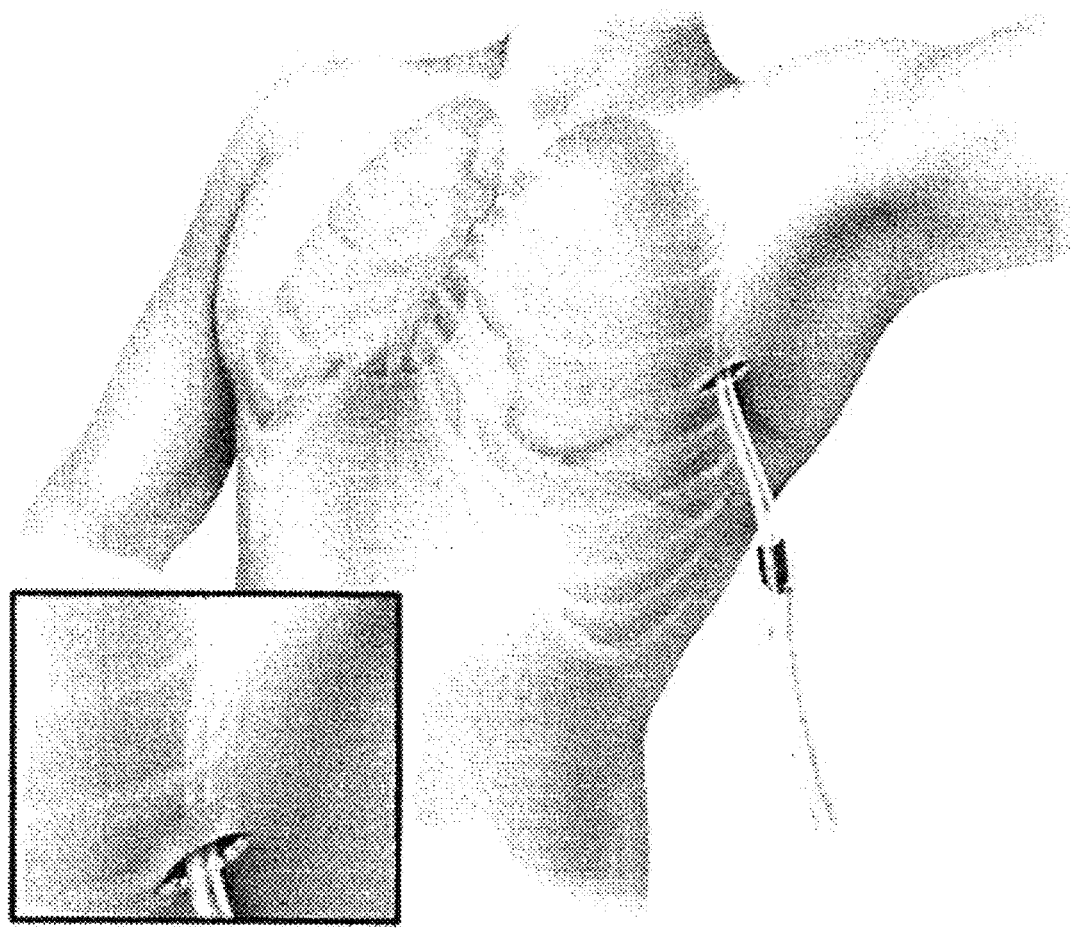
FIG. 34 shows a typical chest tube placement environment and anatomy.

The present invention is directed to a thoracostomy device such as that described herein, that may be applied in the insertion of a chest tube, as shown in FIG. 34, the general steps for which are otherwise known in the medical arts, and are shown generally in FIG. 35.

FIG. 34 shows a typical chest tube placement environment and anatomy.

TABLE 1

Table of product requirements and more specific values.

| Feature Description | Range | Specific |
|---|---|---|
| Material for insertion portion | Biocompatible plastic- surgical stainless steel | Surgical Steel |
| Material for handle | Biocompatible | Plastic |
| Diameter of handle | 1-3 inches | 1.5 inches |
| Length or arms | 3-6 inches | 6 inches |
| Chest tube sizes that tool accommodates | Both of the standard sizes | Both of the standard sizes (20Fr & 40Fr) |
| Hands needed in tract after incision | 0-2 | 0 |
| Additional equipment needed | Fit in Chest Tube Kit- Additional Separate Tool | Fit in Chest Tube Kit |
| No fluid leakage | No fluids out- Less than10 mL | No fluids |
| Width of device + tube when in body* | 10-30 mm | 20 mm |
| Device's ability to be sterilized & reused | One Use - Reusable multiple times | Reusable |
| Movement of tube while removing device | 0-10 mm | 0 mm |

TABLE 1-continued

Table of product requirements and more specific values.

| Feature Description | Range | Specific |
|---|---|---|
| Verification of correct entry point to pleural cavity | Allows for finger sweep-eliminates need for it | Eliminates need for finger sweep |
| Width of tract | 1-2 inches | 1 inch |
| Feature Description | Range | Specific |
| Time reduction to complete procedure per surgeon | 0-50% | 50% |
| Chest tube size accommodation | 28, 32, 36, 40 FR | 28, 32 FR |
| Hands needed to complete procedure | 1-6 | 2 |
| Placement accuracy | 0-100% | 88% |
| Additional equipment to complete procedure (scalpel, kelly's, etc.) | 1-6 | 1 (scalpel) |
| Width of tip of device entering ribs | 5-14 mm | 7 mm tip, 12 mm rib, 12.5 w' tube |
| Product life-time (autoclave) | 1-1000 | 50 cycles (PEEK handle) |
| Handle width | 20-50 mm | 30 mm |

*For adults, tube sizes range 20 Fr to 40 Fr (6.7 to 13.3mm external diameter)

While embodiments and applications of this invention have been shown and described, it would be apparent to those skilled in the art that many more modifications than mentioned above are possible without departing from the inventive concepts herein. It is to be understood that the present disclosure is illustrative only and that changes, variations, substitutions, modifications and equivalents will be readily apparent to one skilled in the art and that such may be made without departing from the spirit of the invention as defined by the following claims.

What is claimed is:

1. A thoracostomy device adapted to be extended into an incision in a patient, comprising:
  (a) A handle portion having a distal end;
  (b) an insertion portion extending through said handle portion and extending from said handle portion distal end, and having a linear portion and a curved terminal portion having a distal end, said insertion portion having opposed substantially continuous first inner and second outer lateral surfaces, said device defining a central axis extending therethrough, wherein said insertion portion includes an atraumatic tip disposed at the distal end, the atraumatic tip includes a flat portion that is perpendicular with respect to the central axis and the flat portion being a length that is between ½ and ⅓ of a diameter of the insertion portion; and
  (c) a continuous channel open at its proximal and distal ends, and extending through said insertion portion and open along a lateral side thereof to said first inner lateral surface, said channel having a medial axis offset from and parallel to said central axis, said channel adapted to guide a tube along said central axis and distally to a position beyond said curved terminal portion distal end, while being adapted to allow a tube to be removed laterally of said open channel, wherein said channel includes an overhang to provide an opening that is narrower than a widest portion of an inner diameter of the channel.

2. The thoracostomy device of claim 1, wherein the width of said handle portion is greater than the width of said insertion portion.

3. The thoracostomy device of claim 2, wherein said handle portion comprises a main portion and a relatively minor distally tapered portion, said tapered portion tapered toward said insertion portion.

4. The thoracostomy device of claim 3, wherein said relatively minor distally tapered portion comprises an offset frustoconical shape.

5. The thoracostomy device of claim 2, wherein the surface of said relatively minor distally tapered portion is continuous with said second outer lateral surface.

6. The thoracostomy device of claim 1, wherein said channel has an internal surface cross-section defining an arc of from about 210 degrees to about 325 degrees.

7. The thoracostomy device of claim 1, wherein said channel has an internal surface cross-section defining an arc of from about 250 degrees to about 290 degrees.

8. The thoracostomy device of claim 1, wherein said linear portion is relatively greater in length than said curved terminal portion, and wherein curved terminal portion distal end is blunt.

9. The thoracostomy device of claim 1, wherein said linear portion is tapered toward said curved terminal portion.

10. The thoracostomy device of claim 1, said linear portion having a longitudinal axis, wherein said curved terminal portion is sufficiently curved so as to provide a deflection of its terminal end from about 5 degrees to about 35 degrees from said longitudinal axis of said linear portion.

11. The thoracostomy device of claim 1, wherein said handle portion has a compartment adapted to contain a scalpel.

12. The thoracostomy device of claim 1, wherein said handle portion additionally comprises a releasable container adapted to contain a flexible tube.

13. The thoracostomy device of claim 12, said releasable container containing a flexible tube.

14. The thoracostomy device of claim 1, wherein said handle portion additionally comprises a light source directed toward said curved terminal portion.

15. The thoracostomy device of claim 1, wherein said continuous channel comprises an inner channel surface comprising a light source directed toward said curved terminal portion.

16. A thoracostomy device adapted to be extended into an incision in a patient, comprising:
(a) a handle portion having a distal end;
(b) an insertion portion extending through said handle portion and extending from said handle portion distal end, and having a linear portion and a curved terminal portion having a distal end, said insertion portion having opposed substantially continuous first inner and second outer lateral surfaces, said linear portion having a longitudinal axis, wherein said curved terminal portion is sufficiently curved so as to provide deflection of its terminal end from about 5 degrees to about 35 degrees from said longitudinal axis of said linear portion; said device defining a central axis extending therethrough, wherein said insertion portion includes an atraumatic tip disposed at the distal end, the atraumatic tip includes a flat portion that is perpendicular with respect to the central axis and the flat portion being a length that is between ½ and ⅓ of a diameter of the insertion portion; and
(c) a continuous channel open at its proximal and distal ends, and extending through insertion portion and open along a lateral side thereof to said first inner lateral surface, said channel having a medial axis offset from and parallel to said central axis, said channel adapted to guide a tube along said central axis and distally to a position beyond said curved terminal portion distal end, while being adapted to allow a tube to be removed laterally of said open channel, wherein said channel has an internal surface cross-section defining an arc of from about 210 degrees to about 325 degrees, wherein said channel includes an overhang to provide an opening that is narrower than a widest portion of an inner diameter of the channel.

17. A thoracostomy device adapted to be extended into an incision in a patient, comprising:
(a) a handle portion having a distal end;
(b) an insertion portion extending through said handle portion and extending from said handle portion distal end, and having a linear portion and a curved terminal portion having a distal end, said insertion portion having opposed substantially continuous first inner and second outer lateral surfaces, said device defining a central axis extending therethrough, wherein said insertion portion includes an atraumatic tip disposed at the distal end, the atraumatic tip includes a flat portion that is perpendicular with respect to the central axis and the flat portion being a length that is between ½ and ⅓ of a diameter of the insertion portion;
(c) a continuous channel open at its proximal and distal ends, and extending through insertion portion and open along a lateral side thereof to said first inner lateral surface, said channel having a medial axis offset from and parallel to said central axis, said channel adapted to guide a tube along said central axis and distally to a position beyond said curved terminal portion distal end, while being adapted to allow a tube to be removed laterally of said open channel, wherein said channel includes an overhang to provide an opening that is narrower than a widest portion of an inner diameter of the channel; and
(d) said handle portion having a compartment adapted to contain a medical instrument, scalpel or a flexible tube.

18. The thoracostomy device of claim, 17 said compartment containing a medical instrument.

19. The thoracostomy device of claim 17, said compartment containing a flexible tube.

20. The thoracostomy device of claim 17, wherein said continuous channel comprises an inner channel surface comprising a light source directed toward said curved terminal portion.

* * * * *